(12) United States Patent
Trinkle et al.

(10) Patent No.: US 11,326,138 B2
(45) Date of Patent: May 10, 2022

(54) CELL CULTURE DEVICE AND METHODS OF USE THEREOF

(71) Applicant: University of Kentucky Research Foundation, Lexington, KY (US)

(72) Inventors: Christine Trinkle, Lexington, KY (US); Ren Xu, Lexington, KY (US); Soroosh Torabi, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 271 days.

(21) Appl. No.: 15/968,262

(22) Filed: May 1, 2018

(65) Prior Publication Data

US 2018/0312792 A1 Nov. 1, 2018

Related U.S. Application Data

(60) Provisional application No. 62/492,540, filed on May 1, 2017.

(51) Int. Cl.
*C12M 1/00* (2006.01)
*C12M 3/00* (2006.01)
(Continued)

(52) U.S. Cl.
CPC ............ *C12M 23/16* (2013.01); *C12M 23/20* (2013.01); *C12M 23/38* (2013.01); *C12N 5/0693* (2013.01)

(58) Field of Classification Search
None
See application file for complete search history.

(56) References Cited

U.S. PATENT DOCUMENTS 8,367,214 B2  2/2013 Ma et al.
2009/0078326 A1  3/2009 Rosario et al.
(Continued)

FOREIGN PATENT DOCUMENTS

CN  104475309 A  4/2015
WO  WO20130156941  10/2013

OTHER PUBLICATIONS

Choi et al., Effective slip and friction reduction in nanograted superhydrophobic microchannels, 2006, Physics of Fluids, 18, 087105 (Year: 2006).*

(Continued)

*Primary Examiner* — Holly Kipouros
(74) *Attorney, Agent, or Firm* — Stites & Harbison PLLC; Sean P. Richie

(57) ABSTRACT

Provided herein is a tissue culture device and a method of forming a tissue culture device. The tissue culture device includes a microfluidic layer including at least one hydrophobic microchannel and a reservoir portion over the at least one hydrophobic microchannel, the reservoir portion including an opening aligned with the at least one hydrophobic microchannel. The method of forming a tissue culture device includes providing a microfluidic layer mold, a reservoir layer mold, and a removable lid mold, filling each of the molds with a device material, curing the device material within the molds, removing the cured device material from the molds to provide a microfluidic layer, a reservoir layer, and a removable lid, and bonding the microfluidic layer to the reservoir layer. A method of culturing tissue with the tissue culture device is also provided herein.

16 Claims, 13 Drawing Sheets

(51) Int. Cl.
C12M 3/06 (2006.01)
C12N 5/09 (2010.01)

(56) References Cited

U.S. PATENT DOCUMENTS

| | | | |
|---|---|---|---|
| 2011/0236970 A1* | 9/2011 | Larsen | C12M 23/12 435/348 |
| 2012/0177881 A1 | 7/2012 | Lee et al. | |
| 2012/0258283 A1 | 10/2012 | Sohn et al. | |
| 2013/0309450 A1 | 11/2013 | Khine et al. | |
| 2014/0018263 A1 | 1/2014 | Levkin et al. | |
| 2014/0093962 A1* | 4/2014 | Ingram | B01L 3/502761 435/396 |
| 2014/0255961 A1* | 9/2014 | Prabhakarpandian | G01N 33/5061 435/13 |

OTHER PUBLICATIONS

Iliescu et al., A practical guide for the fabrication of microfluidic devices using glass and silicon, 2012, Biomicrofluidics, 6, 016505 (Year: 2012).*
Bettinger, C., J.T. Borenstein, and S.L. Tao, Microfluidic Platforms for Evaluating Angiogenesis and Vasculogenesis, in Microfluidic Cell Culture Systems. 2012, Elsevier. p. 385-405.
Cheng, S.-Y., et al., A hydrogel-based microfluidic device for the studies of directed cell. Lab on a Chip, 2007. 7: p. 763-769.
Chrobak, K.M., D.R. Potter, and J. Tein, Formation of perfused, functional microvascular tubes in vitro. Microvascular Research, 2006. 71: p. 185-196.
Chung, S., et al., Cell migration into scaffolds under co-culture conditions in a microfluidic platform. Lab on a Chip, 2008: p. 1-8.
Edmondson, R., et al., Three-Dimensional Cell Culture Systems and Their Applications in Drug Discovery and Cell-Based Biosensors. ASSAY and Drug Development Technologies, 2014. 12(4): p. 207-218.
Solden, A.P. and J. Tien, Fabrication of microfluidic hydrogels using molded gelatin as a sacrificial element. Lab on a Chip, 2007. 7: p. 720-725.
Haessler, U., et al., Migration dynamics of breast cancer cells in a tunable 3D interstitial flow chamber. Integrative Biology, 2012. 4: p. 401-409.
Huang, C.P., et al., Engineering microscale cellular niches for three-dimensional multicellular co-cultures. Lab on a Chip, 2009. 9(12): p. 1740-1748.
Huh, D., et al., Reconstituting Organ-Level Lung Functions on a Chip. Science, 2010. 328.
Kim, M.S., J.H. Yeon, and J.-K. Park, A microfluidic platform for 3-dimensional cell culture and cell-based assays. Biomed Microdevices, 2007. 9: p. 25-34.
Lee, W., et al., On-Demand Three-Dimensional Freeform Fabrication of Multi-Layered Hydrogel Scaffold With Fluidic Channels Biotechnology and Bioengineering, 2010. 105(6): p. 1178-1186.
Ling, Y., et al., A cell-laden microfluidic hydrogel. Lab on a Chip, 2007. 7: p. 756-762.
Liu, K., X. Yao, and L. Jiang, Recent developments in bio-inspired special wettability. Chemical Society Reviews, 2010. 39: p. 3240-3255.

Liu, M. and Q. Chen, Characterization study of bonded and unbonded polydimethylsiloxane aimed for bio-microelectromechanical systems-related applications. J Micro/Nanolith. MEMS MOEMS, 2007. 6(2).
Miller, J.S., et al., Rapid casting of patterned vascular networks for perfusable engineered three-dimensional tissues. Mature Materials, 2012. 11: p. 738-774.
Pluen, A., et al., Diffusion of macromolecules in agarose gels: comparison of linear and globular configurations. Biophysical journal, 1999. 77(1): p. 542-552.
Shin, M.K., S.K. Kim, and H. Jung, Integration of intra- and extravasation in one cell-based microfluidic chip for the study of cancer metastasis. Lab on a Chip, 2011. 11: p. 3880-3887.
Song, J.W., et al., Microfluidic Endothelium for Studying the Intravascular Adhesion of Metastatic Breast Cancer Cells. PLoS ONE, 2009. 4(6): p. e5756.
Tan, S.-H., N.-T. Nguyen, and Y.C. Chua, Oxygen plasma treatment for reducing hydrophobicity of a sealed polydimethylsiloxane microchannel. Biomicrofluidics, 2010. 4(3).
Tibbitt, M.W. and K.S. Anseth, Hydrogels as Extracellular Matrix Mimics for 3D Cell Culture. Biotechnology and Bioengineering, 2009. 103(4): p. 655-663.
Toh, Y.-C., et al., A microfluidic 3D hepatocyte chip for drug toxicity testing. Lab on a Chip, 2009. 9.
Varansi, K.K., et al. Design of Superhydrophobic Surfaces for Optimum Roll-off and Droplet Impact Resistance. in ASME International Mechanical Engineering Congress and Exposition. 2008. Boston.
Vickerman, V., et al., Design, fabrication and implementation of a novel multi-parameter control Microfluidic Platform for Three-Dimensional Cell Culture and Real-Time Imaging. Lab Chip, 2008. 8(9): p. 1468-1477.
Wang, X.-Y., et al., Engineering interconnected 3D vascular networks in hydrogels using molded sodium alginate lattice as the sacrificial template Lab on a Chip, 2014. 14: p. 2709-2716.
Whyman, G., E. Bormashenko, and T. Stein, The rigorous derivation of Young, Cassie-Baxter and Wenzel equations and the analysis of the contact angle hysteresis phenomenon Chemical Physics Letter, 2008. 450: p. 355-359.
Zervantonakis, I.K., et al., Microfluidic devices for studying heterotypic cell-cell interactions and tissue specimen cultures under controlled microenvironment. Biomicrofluidics, 2011. 5.
Limongi, et al., Nanostructured Superhydrophobic Substrates Trigger the Development of 3D Neuronal Networks, Feb. 11, 2013.
Shin, et al., Bio-Inspired Extreme Wetting Surfaces for Biomedical Applications 2016.
Neto, et al., 3D Cell Culture: Fabrication of Hydrogel Particles of Defined Shapes Using Superhydrophobic-Hydrophilic Micropatterns, Sep. 15, 2016.
Tropmann, et al., Completely Superhydrophobic PDMS Surfaces for Microfluidics, May 16, 2012.
Migliaccio, et al., Fabrication of hierarchically structured superhydrophobic PDMS surfaces by CuO casting, Nov. 2014.
Vinogradova, et al., Superhydrophobic textures for microfluidics, 2012.
Cortese, et al. Superhydrophobicity Due to the Hierarchical Scale Roughness of PDMS Surfaces, Langmuir, 2008, 24(6), pp. 2712-2718.

* cited by examiner t = 1s    t = 15s    t = 105s

CELL CULTURE DEVICE AND METHODS OF USE THEREOF

RELATED APPLICATIONS

This application claims the benefit of U.S. Provisional Application Ser. No. 62/492,540, filed May 1, 2017, the entire disclosure of which is incorporated herein by this reference.

GOVERNMENT INTEREST

This invention was made with government support under grant number CMMI-1125722 awarded by the National Science Foundation (NSF) and grant numbers CA20772 and CA209045 awarded by the National Cancer Institute (NCI). The government has certain rights in the invention.

TECHNICAL FIELD

The present invention relates to cell culture methods and articles. In particular, the presently-disclosed subject matter relates to a three-dimensional (3D) cell culture device, methods of forming a cell culture device, and methods for use thereof.

BACKGROUND

In the fields of cell biology and medicine, there is a pressing need for biologically relevant ex vivo cell culture models. Traditional 2D cell culture methods fail to represent the complex mechanics and physiology of the in vivo cell microenvironment, such as dynamic nutrient delivery. As a result, critical cell-cell and cell-extracellular matrix (ECM) interactions are missing, and complex behaviors such as cell migration cannot be reproduced. Animal models, on the other hand, more accurately capture this complexity, although they can have many challenges such as high cost, difficulty to observe with high resolution in real time, and potential ethical issues.

Advancements in 3D cell culture methods show promise for increasing the complexity and biological relevance of in vitro culture microenvironments. In particular, by replacing the stiff, 2D tissue culture substrate with a compliant, three-dimensional analogue of the extracellular matrix, cells are provided with a more physiologically relevant microenvironment. However, current models fail to recreate the biological microvasculature and are often incompatible with established tissue culture, imaging, and biochemical analysis methods.

One attempt to solve these issues involves integrating microfluidics with 2D or 3D cell culture methods, which has made it possible to observe complex cell behaviors ex vivo, such as angiogenesis, chemotaxis and cell migration. But for all the advantages of these methods, widespread adoption has been hindered by usability and repeatability issues. Integration of 3D culture with microfluidics typically involves injecting and curing a cell-hydrogel mixture inside an enclosed microfluidic device, which is a challenging process to multiplex with high repeatability, requires unique equipment not present in many tissue culture labs, and necessitates the development of new, often complex, tissue culture protocols. In addition, the nature of these devices makes it difficult to retrieve cells after culture, precluding the use of post-culture biochemical or histological analyses. For example, while there are existing kidney-on-a-chip and liver-on-a-chip devices, these devices are not compatible with current tissue culture equipment and are difficult/impossible to multiplex. Previous organ-on-a-chip devices also typically utilize a porous membrane to separate different cell types, which robs the cells of chemical and mechanical cell-to-cell signaling that they would see in vivo.

Accordingly, there is a need for devices and methods that provide both ease of use and biological relevance without the pitfalls discussed above.

SUMMARY

This summary describes several embodiments of the presently-disclosed subject matter, and in many cases lists variations and permutations of these embodiments. This summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this summary or not. To avoid excessive repetition, this summary does not list or suggest all possible combinations of features.

The presently-disclosed subject matter provides, in some embodiments, a tissue culture device comprising a microfluidic layer including at least one hydrophobic microchannel and a reservoir portion over the at least one hydrophobic microchannel, the reservoir portion including an opening aligned with the at least one hydrophobic microchannel. In one embodiment, the hydrophobic microchannel comprises a Cassie-Baxter mode surface. In one embodiment, the hydrophobic microchannel comprises a material selected from the group consisting of polydimethylsiloxane (PDMS), polystyrene, surface-treated glass, and combinations thereof. In one embodiment, the hydrophobic microchannel comprises a surface treated surface. In another embodiment, the surface treated surface comprises increased surface roughness. In one embodiment, the hydrophobic microchannel comprises a feature height (h) that is greater than the minimum feature height for sustaining Cassie-Baxter mode ($h_{crit}$), wherein $h_{crit}$ is defined as $$h_{crit} = -\frac{b}{2}\left(\frac{\cos\theta_e + 1}{\cos\theta_e}\right)$$

and b is the width of cavities in the microchannel.

In one embodiment, the reservoir portion comprises a material selected from the group consisting of polydimethylsiloxane (PDMS), polystyrene, surface-treated glass, and combinations thereof. In one embodiment, the reservoir portion and the hydrophobic portion comprise the same material. In one embodiment, the reservoir portion and the hydrophobic portion comprise different materials. In one embodiment, the device is devoid of any material separating the at least one hydrophobic microchannel from the opening in the reservoir portion. In another embodiment, the hydrophobic microchannel prevents a solution in the opening of the reservoir portion from filling an internal portion of the hydrophobic microchannel. In one embodiment, the hydrophobic microchannel is in fluid communication with an inlet and outlet of the reservoir portion. In one embodiment, the at least one hydrophobic microchannel comprises multiple hydrophobic microchannels. In another embodiment, a shape and geometry of the hydrophobic microchannels mimics the shape and geometry of blood vessels in a capillary network.

Also provided herein, in some embodiments, is a method of forming a tissue culture device, the method comprising providing a microfluidic layer mold, a reservoir layer mold, and a removable lid mold, filling each of the molds with a device material, curing the device material within the molds, removing the cured device material from the molds to provide a microfluidic layer, a reservoir layer, and a removable lid, and bonding the microfluidic layer to the reservoir layer. In one embodiment, the microfluidic layer is temporarily covered during the bonding step. In another embodiment, covering the microfluidic layer during the bonding step provides a different hydrophobicity between the microfluidic layer and the reservoir layer. In one embodiment, the device material is selected from the group consisting of polydimethylsiloxane (PDMS), polystyrene, surface-treated glass, and combinations thereof.

Further provided herein, in some embodiments, is a method of culturing tissue, the method comprising providing a tissue culture device comprising a microfluidic layer including at least one hydrophobic microchannel and a reservoir portion over the at least one hydrophobic microchannel, the reservoir portion including an opening aligned with the at least one hydrophobic microchannel; introducing a cell solution into the opening in the reservoir portion; solidifying the cell solution in the reservoir portion; positioning a removable lid over the opening in the reservoir portion; and providing a flow of fluid through at least one hydrophobic microchannel; wherein the hydrophobic microchannel prevents the cell solution from flooding the hydrophobic microchannel during the introducing step. In one embodiment, the fluid comprises cell culture media. In another embodiment, the cell culture media flowing through the at least one hydrophobic microchannel is in direct contact with the cell solution. In a further embodiment, the direct contact provides diffusion-based solute exchange between the cell culture media and the cell solution.

BRIEF DESCRIPTION OF THE DRAWINGS

The presently-disclosed subject matter will be better understood, and features, aspects and advantages other than those set forth above will become apparent when consideration is given to the following detailed description thereof. Such detailed description makes reference to the following drawings, wherein.

Figure 1A:
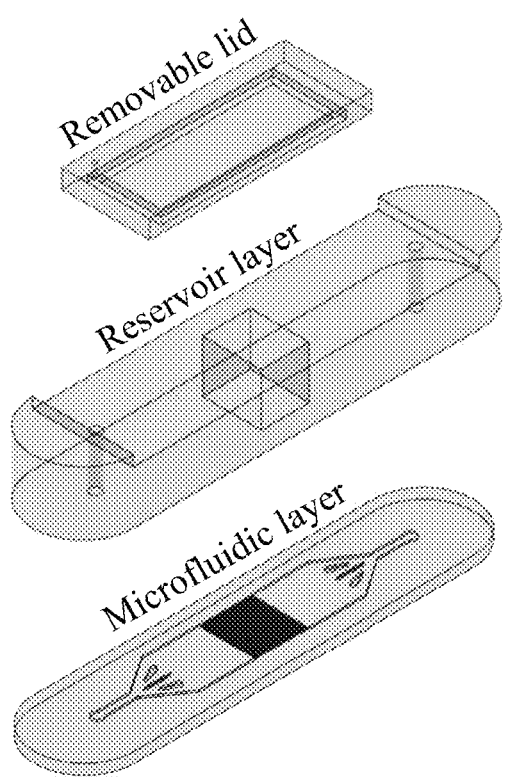
FIGS. 1A-E shows images illustrating a microfluidic tissue culture device according to an embodiment of the disclosure. (A) Shows an exploded view of a microfluidic device illustrating a microfluidic layer, a reservoir layer, and a removable lid. (B) Shows a perspective view of an assembled microfluidic device filled with food coloring to aid in visualization. Scale bar=10 mm. (C) Shows a perspective view of a liquid/hydrogel cell suspension being pipetted into a reservoir of a microfluidic device. The cross-section view along C-C shows an enhanced view of the open microfluidic channels within the microfluidic device. (D) Shows a perspective view of the microfluidic device being incubated to solidify the liquid/hydrogel cell suspension in the reservoir thereof. The cross-section view along D-D shows how the liquid/hydrogel cell suspension does not penetrate the open microfluidic channels due to the Cassie-Baxter nature thereof. (E) Shows a perspective view of a sealed microfluidic device with the solidified hydrogel in the reservoir thereof and a culture media flowing through the open microfluidic channels. The cross-section view along E-E shows an enhanced view of the culture media flowing through the microfluidic channels.

While the disclosure is susceptible to various modifications and alternative forms, specific embodiments thereof have been shown by way of example in the drawings and are herein described below in detail. It should be understood, however, that the description of specific embodiments is not intended to limit the disclosure to cover all modifications, equivalents and alternatives falling within the spirit and scope of the disclosure as defined by the appended claims.

DEFINITIONS

Unless defined otherwise, all technical and scientific terms used herein have the same meaning as commonly understood by one of ordinary skill in the art to which the disclosure belongs. Any methods and materials similar to or equivalent to those described herein can be used in the practice or testing of the present disclosure, including the methods and materials are described below.

Following long-standing patent law convention, the terms "a," "an," and "the" refer to "one or more" when used in this application, including the claims. Thus, for example, reference to "a cell" includes a plurality of cells, and so forth.

The terms "comprising," "including," and "having" are intended to be inclusive and mean that there may be additional elements other than the listed elements.

Unless otherwise indicated, all numbers expressing quantities of ingredients, properties such as reaction conditions, and so forth used in the specification and claims are to be understood as being modified in all instances by the term "about." Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration, percentage, or the like is meant to encompass variations of in some embodiments ±50%, in some embodiments ±40%, in some embodiments ±30%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

All combinations of method or process steps as used herein can be performed in any order, unless otherwise specified or clearly implied to the contrary by the context in which the referenced combination is made.

DETAILED DESCRIPTION

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

Figure 1B:
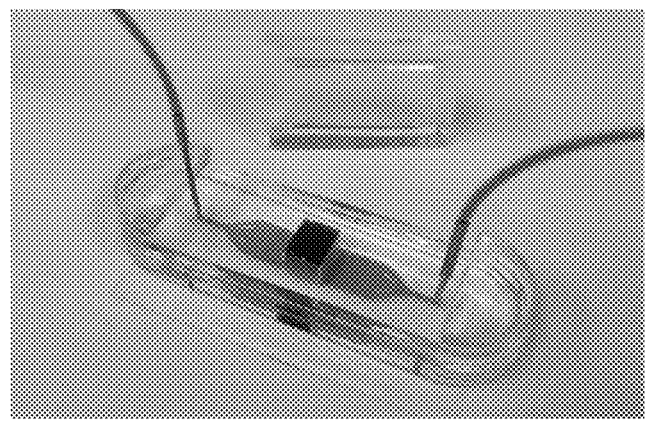

The presently-disclosed subject matter relates to articles and methods for cell culture. In some embodiments, the article includes a three-dimensional (3D) tissue/cell culture device. In one embodiment, the tissue/cell culture device is a microfluidic device including a base portion and a removable lid (FIGS. 1A-B). In another embodiment, the base portion includes a microfluidic layer and a reservoir layer. In a further embodiment, the microfluidic layer is bonded to the reservoir layer to form the base portion, creating a fluid tight seal between the two layers. Alternatively, the microfluidic layer and the reservoir layer may be formed together as a single component.

Figure 1C:
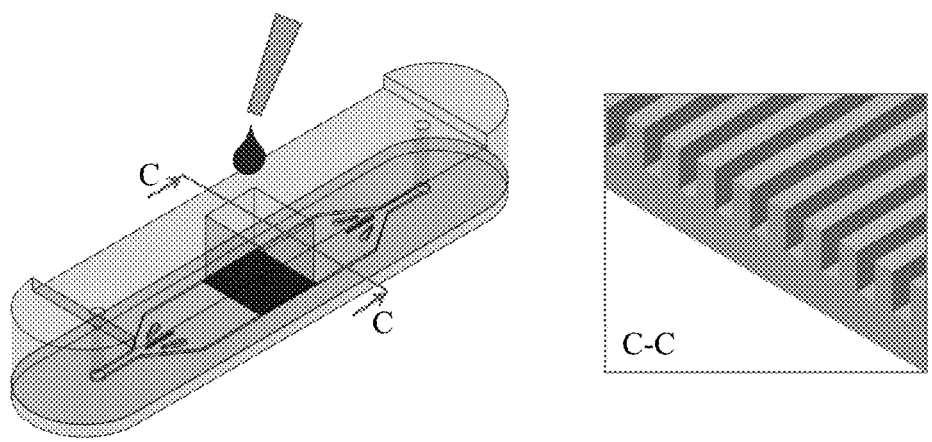

Referring still to FIG. 1A, the reservoir layer includes an opening extending from a top surface to a bottom surface thereof. This opening in the reservoir layer is aligned with one or more microchannels formed in the microfluidic layer and is configured to receive any suitable cell/material/solution therein (FIGS. 1B-C). Suitable cells/materials/solutions include a hydrogel, a hydrogel and cells, cell-embedded collagen, endothelial cell suspensions, tissue-specific cell suspensions, or a combination thereof. In some embodiments, the reservoir layer also includes an inlet and an outlet. When joined with the microfluidic layer, the inlet and outlet are placed in fluid communication with the microchannels to provide fluid flow through the device.

Each of the one or more microchannels includes any suitable shape or geometry for permitting fluid flow therethrough. For example, in one embodiment, the microfluidic layer includes a series of parallel microchannels (FIG. 1C, C-C). In another embodiment, the microchannels are curved, irregular, and/or intersecting. In a further embodiment, a cross-sectional shape of the microchannels may be square, rectangular, rounded, semicircular, triangular, irregular, or include any other suitable shape/geometry. Additionally or alternatively, the size, shape, geometry, and/or spacing may be varied between one or more of the microchannels.

In some embodiments, the one or more microchannels form an integrated microfluidic vasculature. In one embodiment, the integrated microfluidic vasculature is biomimetic, or mimics in vivo vasculature. For example, the geometry of the microchannels may be designed to mimic blood vessels in the body, such as a capillary network. In another embodiment, this integrated biomimetic microvasculature recreates or substantially recreates the in vivo cell microenvironment, providing dynamic nutrient delivery present in in vivo microcirculation. In a further embodiment, the size and spacing of the microchannels may be selected to provide a gradient of nutrients and/or drugs flowing therethrough.

Prior to providing and/or introducing the cells/materials into the reservoir, the microchannels are in an "unenclosed" state, where an uncovered portion of the microchannels faces the reservoir portion. To prevent the microchannels from filling with the solution introduced into the reservoir, the one or more microchannels are formed from any material suitable for resisting the flow of cells and/or other material through the uncovered portion thereof. In some embodiments, for example, the microchannels are formed from hydrophobic materials that provide contact angles sufficient to maintain the cells/other material over the microchannels. Such hydrophobic materials include, but are not limited to, polydimethylsiloxane (PDMS), polystyrene, other hydrophobic polymers, surface-treated glass, any other suitable hydrophobic material suitable for cell contact, or a combination thereof. In one embodiment, the hydrophobicity of the microchannel material is adjusted through surface treatment/modification. In another embodiment, the surface treatment/modification includes increasing a surface roughness of the material, which increases the hydrophobicity thereof. In a further embodiment, the increased surface roughness following surface treatment/modification includes a surface roughness parameter (r), which is the total area of the surface divided by the projected or flat-plane area of the surface, of between great than about 1 to about 10, greater than about 1 to about 9, greater than about 1 to about 8, greater than about 1 to about 7, greater than about 1 to about 6, greater than about 1 to about 5, about 2 to about 10, about 2 to about 8, about 2 to about 6, about 2 to about 5, or any combination, sub-combination, range, or sub-range thereof. Accordingly, in certain embodiments, the hydrophobicity of the same material may differ based upon the amount of surface roughness.

Due to the hydrophobic nature of the microchannels, any suitable cells/materials/cell suspensions may be provided and/or introduced in the reservoir portion without flooding the microchannels. After providing and/or introducing the cells/materials, the microchannels are in an "enclosed" state, where cells or other material in the reservoir portion cover the microchannels without filling them. In the enclosed state, the solidified cells or other materials form a surface over the microchannels that defines a portion of the internal shape of the microchannels while simultaneously permitting fluid flow through the microchannels. Thereafter, any fluid introduced into the device may flow through the microchannels in direct contact with the material in the reservoir. Accordingly, in contrast to existing methods or devices which utilize a barrier or membrane to separate the cells/materials from the microchannels, the instant device permits barrier- and/or membrane-free solute exchange between fluids in the microchannels and the material in the reservoir.

As will be appreciated by those skilled in the art, although the remaining components of the device may be formed from the same material as the microchannels, the disclosure is not so limited and may include any other suitable materials or combination of materials. For example, each of the individual components may be formed from the same material or different materials as the other components. In one embodiment, each of the components is independently formed from any suitable polymer such as, but not limited to, polydimethylsiloxane (PDMS), polystyrene, other hydrophobic polymers, surface-treated glass, any other suitable hydrophobic material suitable for cell contact, or a combination thereof. In another embodiment, the microfluidic layer is formed from a hydrophobic material and the reservoir layer is formed from any other material suitable for contact with a cell or cell solution. In a further embodiment, one or more of the components is optically transparent, such that at least a portion of the device is compatible with standard microscopy techniques. In certain embodiments, the entire device is optically transparent and/or the microchannels are optically matched, which allows cells to be observed during cell culture.

The 3D tissue culture devices disclosed herein provide biologically-relevant tissue culture/organ-on-a-chip models that accurately recreate the in vivo cellular microenvironment, while simultaneously eliminating the cost, imaging challenges, and potential ethical issues associated with animal models. Additionally, the 3D tissue culture devices disclosed herein are compatible with current tissue culture equipment, facilitate easy multiplexing, and are easily parallelized for high-throughput drug screening. In contrast to existing 3D cell culture models, the devices disclosed herein are also compatible with established tissue culture, imaging, and biochemical analysis methods. Furthermore, in contrast to previous organ-on-a-chip devices that typically utilize a porous membrane to separate different cell types, which robs the cells of chemical and mechanical cell-to-cell signaling that they would see in vivo, the devices disclosed herein provide direct cell contact without membranes, thus permitting chemical and mechanical cell-to-cell signaling. Thus, the devices disclosed herein are suitable for uses such as, but not limited to, high-throughput pharmaceutical screening (organ-on-a-chip), tissue engineering, chemical or biochemical detection and analysis, and fundamental cell/tissue studies.

Also provided herein is a method of producing a 3D tissue culture device. In some embodiments, the method includes forming and/or providing a mold for each of the one or more device components, forming the components from the mold, and assembling the components to form the device (FIGS. 2A-G). In one embodiment, for example, the method includes microfabricating reusable molds for each of the components, pouring liquid polymer into the completed molds, curing the polymer, and then removing the polymer components from the molds. Next, the polymer reservoir and microfluidic layers are bonded using any suitable bonding technique, such as, but not limited to, oxygen plasma treatment. Without wishing to be bound by theory, it is believed that exposure to oxygen plasma treatment may increase the hydrophilicity of certain polymers, such as native PDMS. Accordingly, in some embodiments, the microfluidic channels in the microfluidic layer are temporarily covered during the plasma treatment to maintain hydrophobicity. After bonding the reservoir and microfluidic layers, the removable lids are pressed against a top surface of the reservoir layer to draw a vacuum caused temporary sealing of the lid against the device.

In some embodiments, the requisite geometry of the microfluidic platform may be formed using high-throughput manufacturing methods. Suitable high-throughput manufacturing methods include, but are not limited to, hot-embossing or injection moulding. When using these high-throughput manufacturing methods, the bonding step disclosed above in the method of producing a 3D tissue culture device is not necessary. Similarly, without a bonding step, the step of covering the microchannels during bonding is not necessary. In certain embodiment, such methods generate the necessary surface energy using common tissue culture materials, such as polystyrene. Accordingly, these features make this an attractive concept for integration into commercially-available multi-well tissue culture plates.

A tissue culture method is also contemplated by the instant disclosure. In some embodiments, the tissue culture method includes first providing a 3D tissue culture device having a reservoir arranged and disposed to receive a solution and at least one microchannel facing the reservoir.

Next, the method includes providing and/or introducing the solution, such as a hydrogel and/or cell solution, into the reservoir, the solution covering the at least one microchannel without entering the microchannel, such that the solution defines at least a portion of the interior shape of the at least one microchannel. The solution is then solidified within the reservoir, and the reservoir is sealed with the removable lid to reduce or eliminate media evaporation. After sealing the reservoir with the removable lid, a fluid flow is provided through the at least one microchannel, the fluid being in direct contact with the at least one cell covering the microchannels to facilitate nutrient delivery and cell-to-cell communication.

As will be appreciated by those skilled in the art, the cell solution may include any desired cell type. For example, the cell solution may include a hydrogel, endothelial cells, other tissue-specific cell lines, or a combination thereof. Additionally, in some embodiments, the fluid flowrate through the microfluidic channels may be selected and/or varied for different cell types and/or to model different organ types. Accordingly, the presently-disclosed devices and methods facilitate the study of individual cell and tissue types (e.g., endothelial barrier function), as well as multiple cell and tissue types. Additionally or alternatively, the devices and methods disclosed herein may provide multiplexing on multi-well plate platforms.

In some embodiments, the removable lid reversibly seals the reservoir portion, facilitating easy recovery of cured or uncured cells/materials after culture. In one embodiment, this easy recovery of cells/materials facilitates further histological and/or biochemical analysis. Thus, when the integrated microfluidic vasculature is combined with biochemical and/or morphological analysis of the cell culture site, the tissue culture device disclosed herein provides a tuneable, biomimetic platform for high resolution study of cell behavior.

The presently-disclosed subject matter is further illustrated by the following specific but non-limiting example. The following example may include compilations of data that are representative of data gathered at various times during the course of development and experimentation related to the presently-disclosed subject matter.

EXAMPLE

Figure 1D:
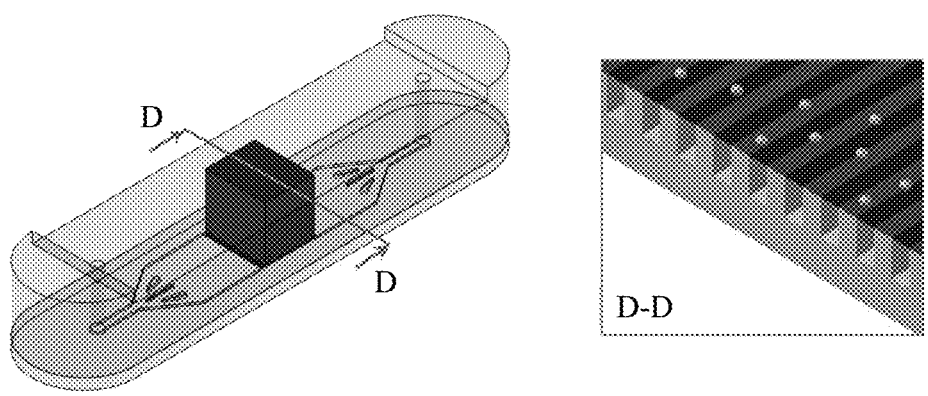
Figure 1E:
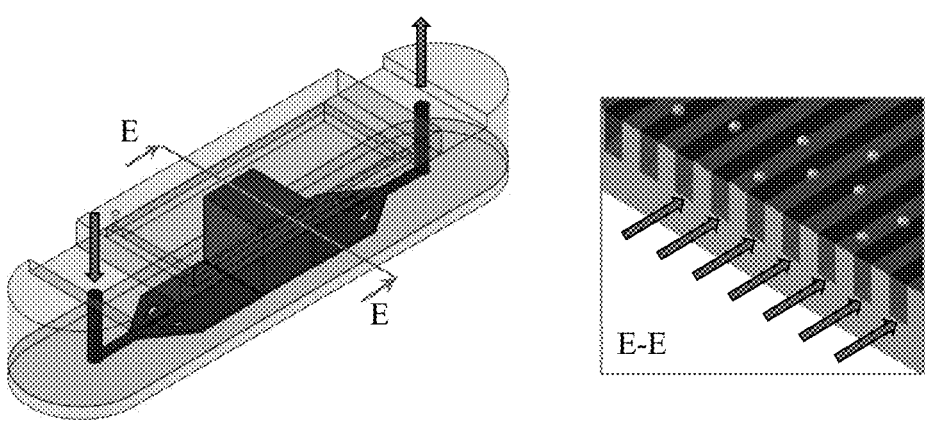

This example demonstrates a novel method of using topographically-induced entrapment of gas to integrate 3D cell culture into a microfluidic platform. The integration of the 3D cell culture is accomplished by creating a microfluidic device that contains an array of open microchannels at the bottom of a macroscale well (FIGS. 1A-B). The topography of these microchannels serves as engineered surface roughness, making it energetically unfavorable for liquid to penetrate the microchannels from above. Therefore, a liquid hydrogel-cell suspension can be pipetted directly into the wells—in a manner identical to that used in standard cell culture—without flooding the microchannels below (FIGS. 1C-D). The cured hydrogel serves as the fourth wall in the microfluidic channels such that fluid pumped through the channels is in direct contact with the hydrogel surface. This, combined with a removable lid which is used to seal the top of the well, provides a fluid path for flowing media through the microchannels (FIG. 1E).

The resulting microfluidic device creates an effective, integrated model that can be used for vascularized 3D cell culture on a chip, where convective flow through the microchannels combined with diffusion-based solute exchange between the channels and cell-laden hydrogel, mimics solute delivery in microvasculature and interstitial fluid in vivo. This biomimetic microvasculature recreates the in vivo cell microenvironment while enabling biochemical and morphological analysis of the cell culture site.

Materials and Methods

Device Fabrication

The microfluidic devices were made of three polydimethylsiloxane (PDMS) components: the reservoir layer, microfluidic layer, and removable lid (FIG. 1A). Each of these components were fabricated separately using soft lithography, and then the reservoir and microfluidic layers were plasma bonded together to create the complete device shown in FIG. 1B.

Figure 2A:
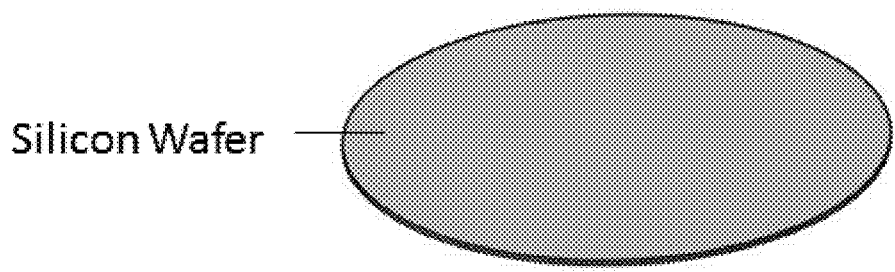
FIGS. 2A-G shows images illustrating stepwise fabrication of a microfluidic device with soft lithography according to an embodiment of the disclosure. (A) Shows an image of a silicon wafer. (B) Shows an image of the silicon wafer after being spin-coated with a layer of SU-8 photoresist. (C) Shows an image of the SU-8 photoresist coated wafer being selectively crosslinked using UV light through a photomask. (D) Shows an image illustrating a positive set of features on the silicon after removal of the uncrosslinked SU-8. (E) Shows an image illustrating liquid PDMS being poured onto this positive mold. (F) Shows an image of the final PDMS material after being cured in an oven and then removed from the mold. (G) Shows an image illustrating the microfluidic and reservoir layers after being plasma-bonded together. The reservoir layer and removable lid components are fabricated in a similar manner.
Figure 2B:
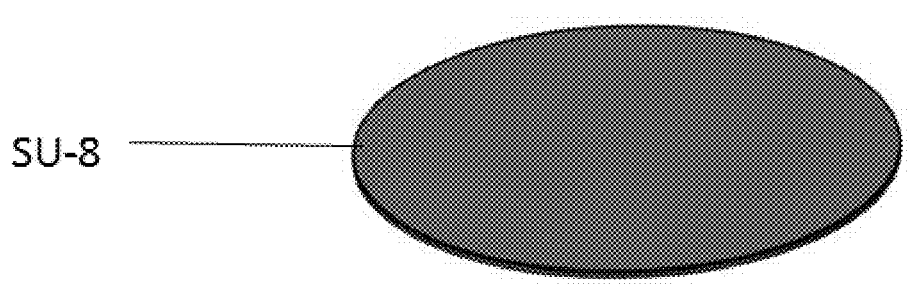
Figure 2C:
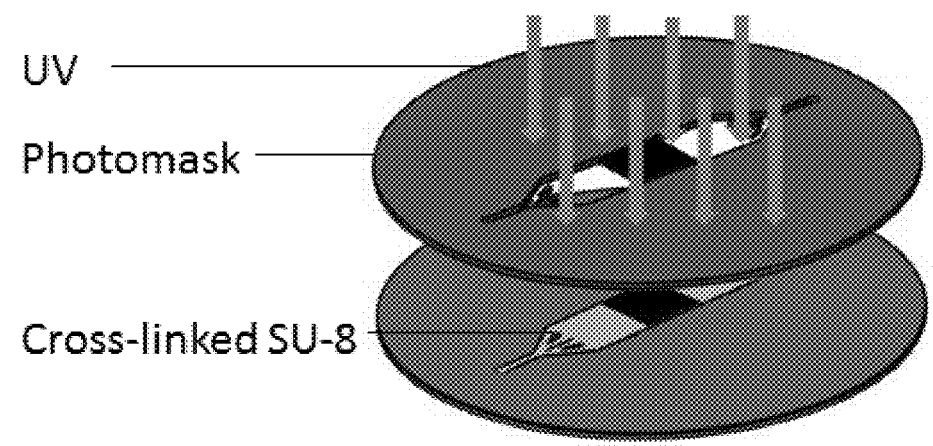
Figure 2D:
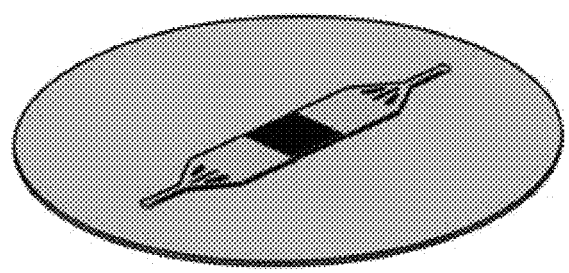

To generate the mold for the microfluidic layer, a 200 µm thick layer of photoresist (SU-8 3050, MicroChem) was spin-coated onto a flat silicon wafer at 1500 rpm for 30 seconds (FIGS. 2A-B). Next, the spin-coated wafer was prebaked (1 min at 65° C., 60 min at 95° C., and 1 min at 65° C.) and the photoresist was exposed to UV light through a patterned photomask causing crosslinking of the exposed SU-8 (FIG. 2C). The wafer was then post-baked (1 min at 65° C. followed by 5 min at 95° C.) and subsequently agitated in SU-8 developer for 10-15 minutes in order to remove uncrosslinked SU-8 (FIG. 2D). After agitating, the wafer was rinsed in isopropanol alcohol (IPA 70% in water, Sigma-Aldrich) and dried with nitrogen gas. Once dry, it was exposed to Trichlorosilane (Sigma-Aldrich) under vacuum for 40 minutes to produce a hydrophobic surface. Cast sheets of acrylic (McMaster-Carr) were laser-cut to form gaskets, which were clamped to the silicon wafers in order to complete the molds. Similar molds were made for the reservoir layer and removable lid components.

Figure 2E:
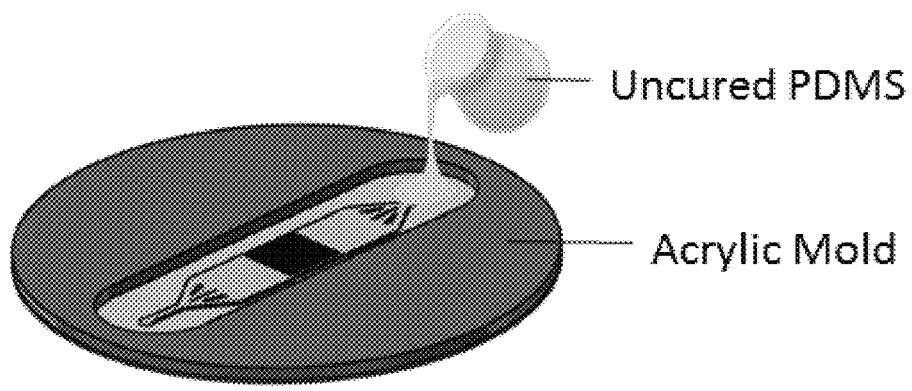
Figure 2F:
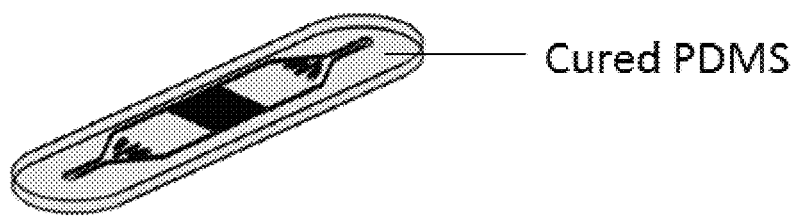

PDMS components were cast by vigorously mixing PDMS base and curing agent (Sylgard 184, Dow Chemical) at a 10:1 ratio, followed by degassing under vacuum for 1 hour. The degassed liquid PDMS was poured into the completed molds and cured for 2 hours in a 65° C. oven (FIG. 2E). After curing, the molds were removed from the oven and allowed to cool to room temperature; then, the final PDMS components were peeled from the molds (FIG. 2F).

Figure 2G:
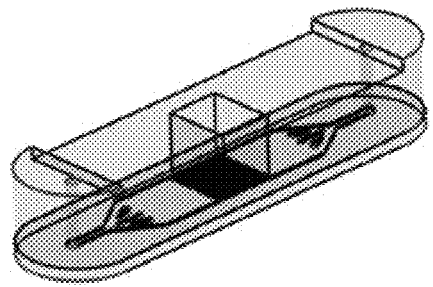

The complete microfluidic devices were assembled by permanently bonding the reservoir and microfluidic layers together using oxygen plasma treatment (FIG. 2G). In order to maintain the hydrophobicity and prevent exposure of the microfluidic channels to oxygen plasma treatment, which makes PDMS more hydrophilic, the top surfaces of the microfluidic channels were temporarily covered during the plasma treatment steps. After this, the flat (feature-free) side of the microfluidic layer was plasma bonded to a glass cover slip to add mechanical rigidity.

Removable PDMS lids were made using the same PDMS casting process as the other components. The PDMS removable lids were thick blocks of material that contained a narrow rectangular groove on one side that was larger than the cross-section of the reservoir. Pressing this side against the flat top surface of the microfluidic device and drawing a vacuum caused temporary sealing of the lid against the microfluidic device. After experiments were complete, removal of the lid simply required removing the vacuum.

Wettability Mode Observation

Visual identification of surface wettability modes was performed using 1.5 wt % agarose on PDMS surfaces with periodic surface features. All PDMS surfaces were fabricated using standard soft lithography of SU-8/silicon molds, as described above. In some cases, a small amount of blue silicone pigment (Silic-Pig, Smooth-On) was added to the PDMS prior to the degassing step in order to aid in visualization. Low-melting point agarose powder (Promega) was dissolved in 77° C. DI water at 1.5 wt %; 1.0 wt % of Rhodamine B solution (Fluka Analytical) was added to the heated agarose solution in order to aid in visualization. 150 µL of this solution was pipetted onto PDMS micropatterned surfaces which had been preheated to 77° C. in order to prevent immediate gelation of the agarose upon contact. The surfaces were then allowed to cool to room temperature to cause gelation of the agarose. After the agarose solidified, a sharp razor blade was used to bisect the agarose and PDMS microchannels to obtain a cross section that could be observed under a microscope.

Contact Angle Measurement

PEGDA gel was made by a mixture of 25 wt % of PEGDA powder (Sigma), 35 mM of TEA(triethanolamine) (Acros), and 35 mM of VP(1-vinyl-2-pyrrolidinone) (Sigma), diluted in PBS (Sigma). Gelatin Methacryloyl gel was made by mixing 3 wt % GelMA, 1 wt % PEGDA powder, 35 mM TEA, and 35 mM VP in PBS. The high concentration collagen solution (37 vol %) was made by mixing F12 basic medium (Sigma-Aldrich), 10×DMEM (Sigma-Aldrich), 1M NaOH (Sigma-Aldrich) and collagen (Bovine collagen type I, 3.18 mg/ml, Angio-Proteomie) in a 680:43:4:434 ratio. For the low concentration collagen (70 vol %), the respective ratio was 340:43:4:434. Agarose gel was made by dissolving Agarose powder (Agarose, LMP, analytical grade, Promega) in 77° C. DI water at 1.5 wt %. The contact angle measurements were conducted by applying a 10 µl drop of each liquid solution on a flat PDMS surface and using an optical goniometer to read the contact angle.

Convective Flow and Diffusion Observation

To illustrate a dynamic solute exchange between the hydrogel and the fluid in the microchannels, a liquid suspension of 1.5 wt % agarose in DI water was pipetted into the open reservoir of the microfluidic device. After solidification of the agarose, water containing 1.0 wt % rhodamine was introduced into the inlet using a syringe pump at a constant volumetric flowrate of 25 µL/min. Time-lapse images were taken every 30 seconds using a TI-E Nikon microscope and the fluorescent intensity was measured in the resulting images using NIS-Elements software in order to track the rhodamine diffusion from the channels into the agarose hydrogel. The experiments were repeated with a solution of 2,000 kDa FITC-dextran at 0.6 mg/mL in DI water at the same flowrate.

In a separate set of experiments designed to demonstrate convective flow in the microchannels, a liquid suspension of 1.5 wt % agarose in DI water was pipetted into the open reservoir of the microfluidic device and solidified. After solidification, a suspension of 20 µm diameter fluorescent microspheres (Phosphorex, Inc.) in DI water was introduced into the fluidic inlet at a constant volumetric flowrate of 2 µL/min. Time lapse images were taken every 400 milliseconds to track the motion of the microspheres in the microfluidic channels. NIS-Elements software was used to calculate the average velocity of the microspheres in the microchannels.

3D Cell Culture in Microfluidic Device

The PDMS microfluidic devices were sterilized prior to use with cells using a two-step process. First, each device, including the fluidic pathways and cell reservoir, were rinsed with 70% ethanol (Sigma-Aldrich) and then placed in a 60° C. oven for 20 minutes to dry. Then, immediately prior to introducing the cell/hydrogel suspension, each device was exposed to UV light for 30 minutes.

For all cell experiments, MDA-231 Luc-GFP cells were suspended in a collagen solution at a concentration of 40000 cells/mL. The collagen solution was made by F12 basic medium (Sigma-Aldrich), 10×DMEM (Sigma-Aldrich), 0.2M NaOH (Sigma-Aldrich) and collagen (Bovine collagen type I, 3.18 mg/ml, Angio-Proteomie) in a 680:43:43:434 ratio on ice. For cell culture in the microfluidic devices, 120 µL of the collagen-cell suspension was carefully pipetted into the cell culture reservoir and then cured in the incubator for 40 minutes at 37° C. Once the collagen was cured, a removable lid was added to each device and sealed by using a syringe to draw a vacuum through the vacuum port. Media was continuously supplied through the microfluidic inlet ports at a rate of 2 µL/min using a syringe pump. To obtain the proliferation rate and number of cells, luciferase was measured using an IVIS imaging system.

Results and Discussion

A number of methods have been previously demonstrated to integrate 3D cell culture and microfluidics, including the use of permeable membranes as boundaries. The use of permeable membrane to separate cell culture and fluid flow is similar to the use of membranes in transwell plates. For example, in such methods, a thin (~10 µm) membrane with periodic perforations, typically 1-5 um in diameter, is used to isolate cell culture on one side of the boundary until the cells have adhered and/or hydrogel has gelled. At this point, fluid can be introduced to the opposing side of the membrane, and solute exchange occurs through the membrane perforations. While much insight has been gained using this method, the membrane is both thicker—by an order of magnitude—and stiffer—by several orders of magnitude—than a typical capillary wall in vivo. Therefore, the presence of the membrane will alter both the diffusive exchange of solutes between the fluid and cells, and may alter physiological properties of cells cultured in contact with it.

Boundary-free integration of 3D cell culture and microfluidics has also been demonstrated previously, notably by in situ patterned gelation of hydrogel inside microchannels or by molding the hydrogel itself to include microfluidic flow pathways. The former method uses either defined flow pathways or UV radiation to trigger gelation only within specific regions inside a confined microchannel. This method offers excellent patterning resolution and has been particularly useful in elucidating mechanisms in cell migration. However, the complexity of this method, requirements for equipment often not available in most cell culture labs, and difficulty in retrieving cells after culture, make it challenging to implement in many applications. Molding microfluidic channels directly into hydrogels bypasses the integration issue entirely and can even be used to generate three-dimensional vascularized constructs when used in concert with a sacrificial material, but this method requires specialized equipment for generating these constructs, and the low elastic modulus of the hydrogel material limits the size and resolution of the microchannels.

In view thereof, the instant inventors have developed a microfluidic device that provides boundary-free integration of microfluidics and 3D cell culture by leveraging the entrapped-gas phenomenon that occurs in high-roughness surfaces. In this device, open microchannels serve as an engineered surface "roughness," so cell-hydrogel suspensions can be directly pipetted onto the surface and the entrapped-gas phenomenon prevents the hydrogel from penetrating the microchannels. After gelation, the hydrogel surface forms the "fourth wall" of the channels in the microfluidic network, and fluid can be freely pumped into the channels. Without a physical boundary, the device allows exchange of solutes with the cells through both convective fluid flow and local diffusion—similar to solute exchange that occurs in vivo due to circulation and interstitial transport.

Entrapped-Gas Effect in Cassie-Baxter Surfaces

Figure 3A:
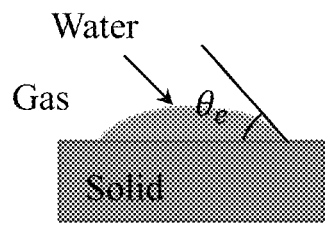
FIGS. 3A-C show images illustrating how surface topography and surface energy determines Wenzel or Cassie-Baxter wetting modes. (A) Shows an image illustrating contact angles for hydrophilic (wetting) and hydrophobic (nonwetting) surfaces. (B) Shows a schematic of Wenzel and Cassie-Baxter modes; in the former, the liquid wets the entire surface, while in the latter, gas becomes entrapped beneath the liquid layer, forming a complex three-phase system. (C) Shows micrographs illustrating Wenzel and Cassie-Baxter wetting modes in an agarose/PDMS system. A liquid suspension of agarose (dyed red) was introduced to the PDMS surface (dyed blue), and then cured and sectioned for visualization. Scale bars=50 µm.
Figure 3A:
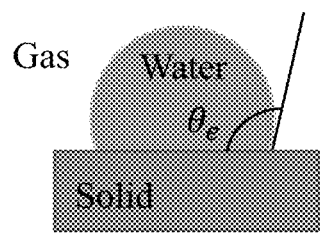

When a liquid droplet comes to contact with a flat, homogeneous, solid surface, there are three different interfacial energy values that determine the equilibrium shape of the droplet. The surface tension between the solid and gas phases ($\gamma_{SG}$), the solid and liquid phases ($\gamma_{SL}$), and the liquid and gas phases ($\gamma_{LG}$) determine the angle of contact between the solid and liquid phases ($\theta_e$), as shown in FIG. 3A. For smooth surfaces, the wettability in terms of $\theta_e$ is governed by Young's equation:

$$\gamma SG - \gamma SL - \gamma LG \cos(\theta_e) = 0$$

This contact angle is defined for a set of solid, liquid and gas materials (e.g., $\theta_e = 104° \pm 3°$ for PDMS); and if it is greater than 90° for water, the surface is referred to as hydrophobic.

Figure 3B:
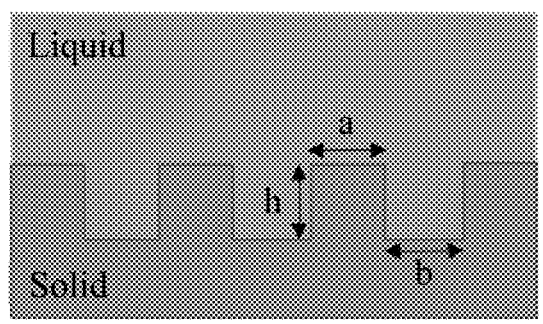
Figure 3B:
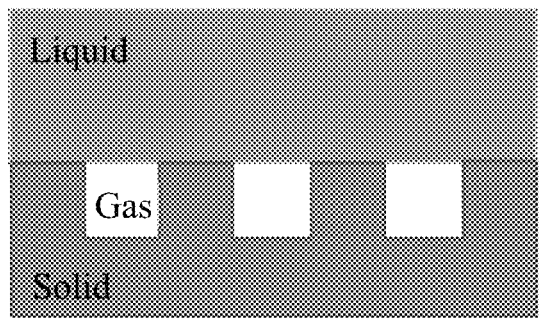

If the solid material has an inherent surface roughness, a liquid droplet introduced onto this surface will either completely wet the surface, displacing all gas and forming a continuous solid-liquid boundary (Wenzel mode), or it will only partially wet the surface, leaving pockets of gas trapped beneath the liquid and forming a complex series of solid-liquid, solid-gas, and gas-liquid boundaries (Cassie-Baxter mode), as shown in FIG. 3B. The favorability of either Cassie-Baxter or Wenzel mode for a given surface is governed by a combination of the microscale surface topography of the solid and the interfacial energy between the phases present.

For materials with a high contact angle, it is energetically favorable to minimize the interfacial area between the liquid and solid phases. Surfaces with high roughness have a larger effective surface area than an equivalent flat surface. To minimize the solid-liquid interfacial area, the liquid often becomes pinned to the highest elevation features on the surface, trapping air pockets beneath the liquid in classic Cassie-Baxter (CB) mode. Cassie-Baxter mode surfaces exhibit much higher observed contact angles compared to Wenzel mode surfaces made of the same material. As such, in order to create open microchannels adjacent to a cell-laden hydrogel in the instant example, the geometry was designed such that it would be energetically unfavorable for liquid collagen to fill the microchannels. More specifically, the stable entrapment of gas in open-top PDMS microfluidic channels due to the trapped gas phenomenon in CB surfaces was exploited to create boundary-free integration of hydrogels with microchannels.

Figure 3C:
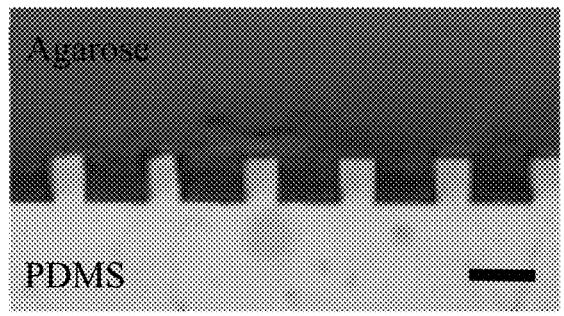
Figure 3C:
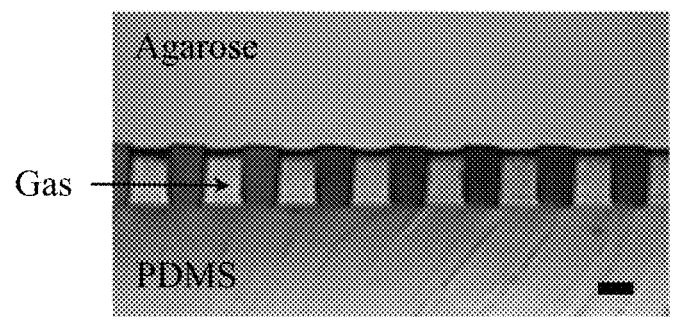

In order to experimentally verify the formation of CB and Wenzel boundaries in PDMS surfaces, a series of SU-8/silicon surfaces with controlled, periodic topography were generated using photolithography and then replicated using soft-lithographic patterning of PDMS. Agarose was dissolved in water at 77° C. at 1.5 wt %, pipetted onto the PDMS surfaces and then cooled to room temperature, causing gelation of the hydrogel. Cross-sections of PDMS and agarose surfaces prepared in this manner are shown in FIG. 3C. In high roughness surfaces, there is clear evidence of gas entrapment, indicative of the CB mode, while complete surface wetting occurs in the lower roughness surfaces.

The theoretical transition between CB and Wenzel modes occurs at the following boundary:

$$\cos \theta_e = \frac{-f_2}{r - f_1} \quad (1)$$

where $f_1$ is the percentage of the surface area under the liquid that is in contact with a solid surface and $f_2$ is the percentage of the surface area under the liquid that is in contact with gas. The roughness parameter, r is defined as the ratio of the total surface area of the solid to the projected surface area of the solid. For surfaces of the type shown in FIG. 3A, where the liquid interface is entirely in one plane, these parameters can be defined as:

$$f_1 = \frac{a}{a+b} \quad f_2 = \frac{b}{a+b} \quad r = \frac{a+b+2h}{a+b}$$

This makes it possible to express the transition between CB and Wenzel modes as a linear relationship between the minimum feature height that will sustain CB mode ($h_{crit}$) and the width of the cavities (b) for a given material:

$$h_{crit} = -\frac{b}{2}\left(\frac{\cos\theta_e + 1}{\cos\theta_e}\right) \quad (2)$$

The contact angle for PDMS on water is approximately $\theta_e = 104°$. Using the above relationship, this means that the feature height (h) needs to be at least about 1.6 times the gap dimension in order to induce CB mode on a PDMS surface.

Figure 4:
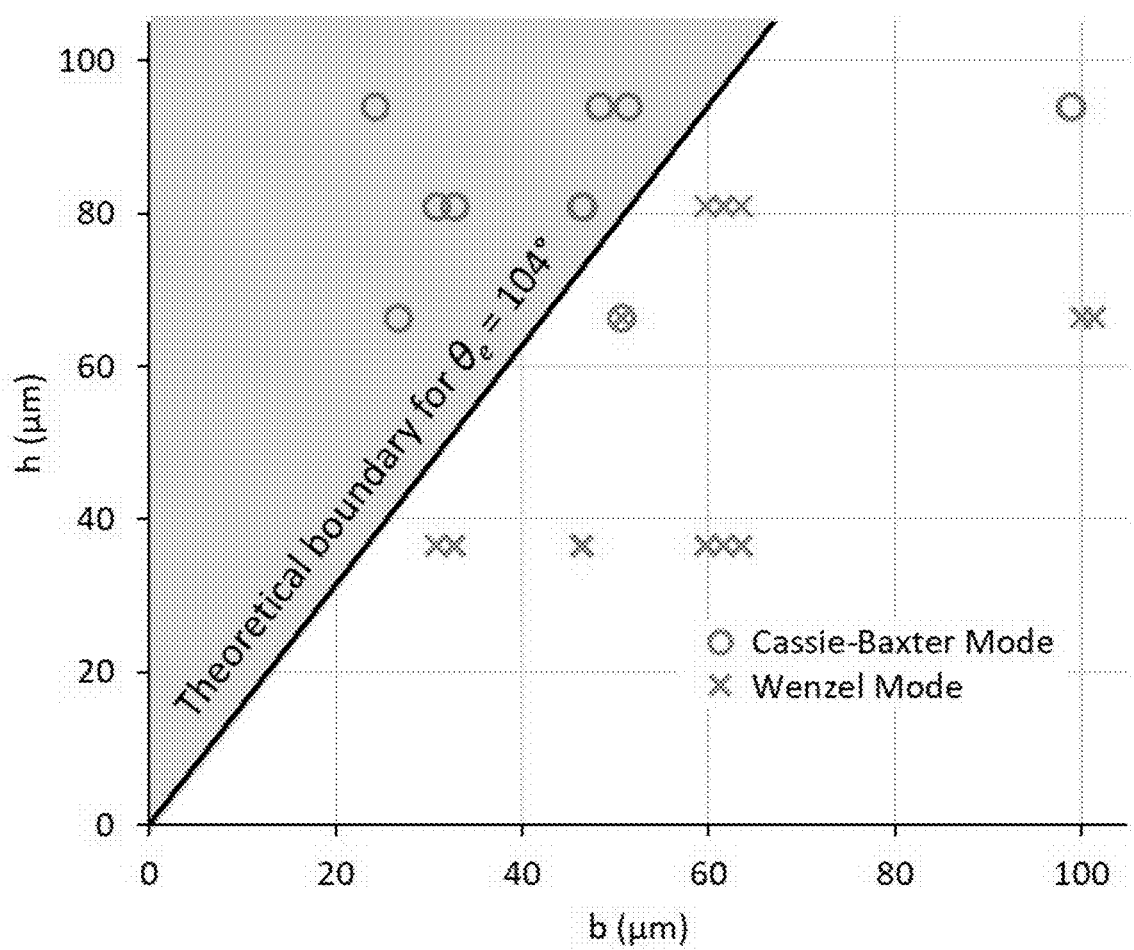
FIG. 4 shows a graph illustrating wettability modes for a variety of microfabricated surface topographies. Solid line depicts theoretical boundary between Wenzel (white) and Cassie-Baxter (grey) modes for Young's Angle corresponding to PDMS ($\theta_e \approx 104°$). Discrete points show experimental data for agarose hydrogel on PDMS.

This theoretical boundary is shown graphically in FIG. 4, along with a number of experimental data points. The solid line depicts the theoretical boundary between Wenzel and Cassie-Baxter modes for the contact angle associated with water on PDMS. Each data point represents a PDMS surface that was tested using 1.5% agarose as in the manner shown in FIG. 3B; circles represent experiments where Cassie-Baxter mode was observed and an x represents experiments where Wenzel mode was observed. For all experimental cases in the region where theory predicts CB mode to occur ($h > h_{crit}$), CB mode was observed without exception. In the predicted Wenzel region, the vast majority of the experimental points agreed with theory, with only two outliers. Therefore, equation (2) appears to be a good predictor of the boundary between the two modes.

The experimental outliers in FIG. 4 may be partially explained by the assumptions used in derivation of equation (2). An interesting observation about equation (2) is that wetting mode is dependent only on the contact angle, h, and b, while the a dimension does not appear. As shown in FIG. 4, in an area close to the transition line, there was one repeatable case in which the same pair of h and b, but a different value of a, caused different wettability modes to occur. For the same h and b, the higher a value corresponds to Wenzel mode, where the lower a value results in a Cassie-Baxter mode. Therefore, it can be a matter of interest to investigate the dependence of mode transition on a that has not been captured in the current model. These deviations from the predicted mode could be caused by assumptions in the model derivation that do not account for other factors such as gravitational and pressure effects.

The contact angle used in these calculations was for water on flat PDMS. Five hydrogel precursor solutions were tested on PDMS; of those five, three displayed contact angles similar to that of water, while two were slightly lower (Table 1). Lower values of $\theta_e$ lead to an increase in the slope of the transition line shown in FIG. 4, which means that it requires taller features to stably generate CB mode in periodic surfaces.

TABLE 1

Contact Angle of Liquids on PDMS

| Liquid | Contact Angle |
|---|---|
| Water | 102.4° ± 3.3° |
| Collagen (high) | 101.4° ± 3.8° |
| Collagen (low) | 99.0° ± 4.6° |
| PEGDA 3500 | 93.4° ± 5.5° ** |
| GelMA | 97.4° ± 8.1° |
| Agarose (1.5%) | 90.8° ± 4.5° ** |

** Statistically different from water value ($p < 0.05$)

Microfluidic-Hydrogel Integration Using CB Surfaces

The knowledge gained from the previous analysis was used to design a series of open microchannels that result in Cassie-Baxter mode when hydrogel is pipetted onto the top surface. The combination of geometry and contact angle pins the interface, preventing the microchannels from flooding. When the hydrogel is solidified during incubation, the formation of the microchannels' circumferential area is finalized; with the bottom, left and right side walls made of PDMS, and the top wall is comprised of the hydrogel material. This creates an open fluid path for convective flow through the microchannels, combined with free exchange of solutes to and from the hydrogel via diffusion.

Figure 5:
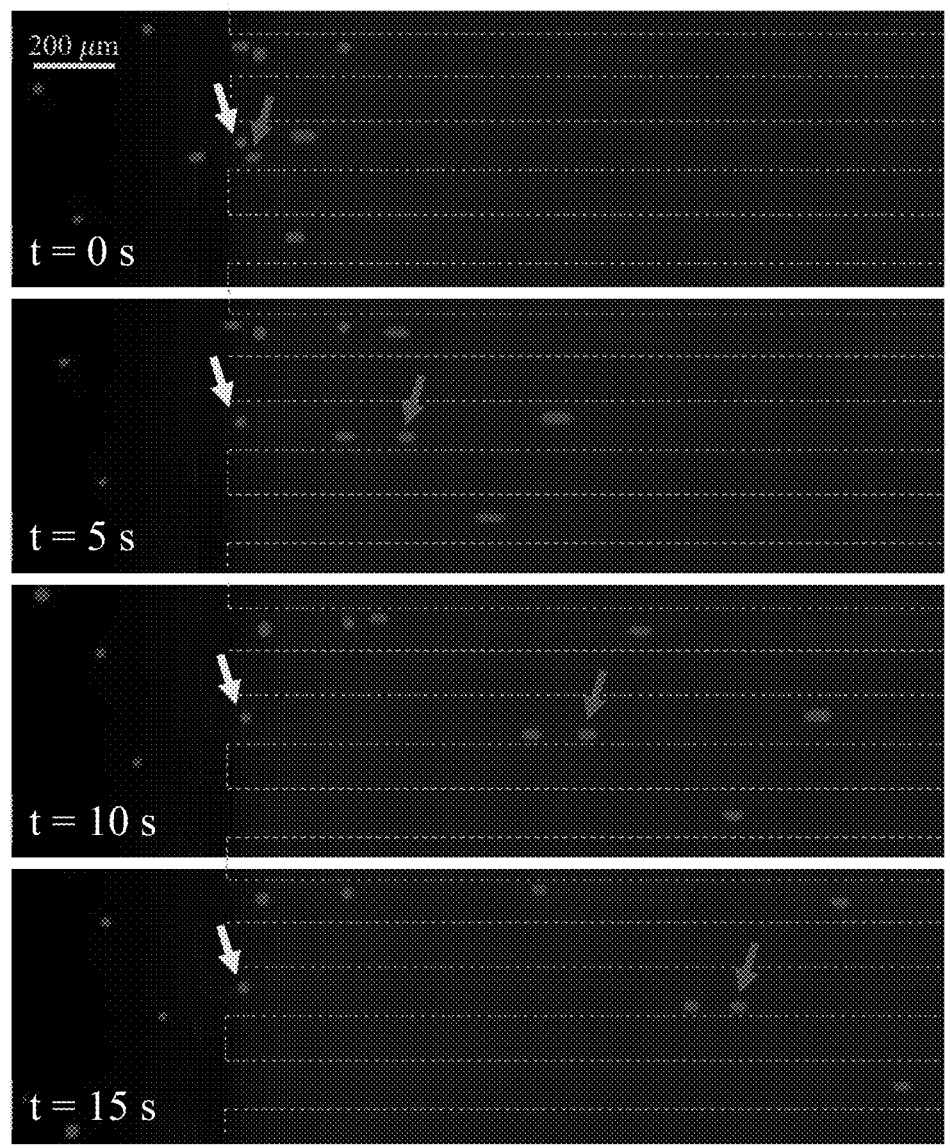
FIG. 5 shows images illustrating fluid flow and solute delivery through microfluidic channels, moving from left to right. Together, the images provide time-lapse micrographs showing 20 µm diameter microspheres flowing through microchannels. Some microspheres became attached to the hydrogel surface (yellow arrows), but all channels contained freely-flowing microspheres (red arrows), demonstrating an open fluid path below the hydrogel. Dashed lines represent boundaries of PDMS microfluidic channels.

In order to demonstrate stable CB formation and unobstructed convective flow in the microchannels of the microfluidic device, liquid agarose solution was pipetted into the reservoir and solidified; then, a dilute solution of 20 µm diameter fluorescent microspheres in water was introduced into the fluidic inlet at a flowrate of 25 µL/min. Time lapse images of the microchannels, shown in FIG. 5, demonstrate that while a few microspheres became attached to the surface of the agarose (yellow arrows), the majority of microspheres flowed freely through the channels (red arrows) from left to right at an average velocity of 64±14 µm/s. Moving microspheres were observed in all channels in the device. Based on the known geometry of the microchannels below the agarose in the device (25 parallel channels, each 200 µm×100 µm), the theoretical average velocity in the channels should be approximately 62 µm/s. The close agreement between the theoretical value and observed velocity of the microspheres implies that all of the microchannels were open to unrestricted fluid flow after the agarose solidified.

Another vital attribute of successful hydrogel/microfluidic integration is diffusion-based exchange of solutes between the hydrogel and the fluid in the microchannels. In order to demonstrate this in our device, 1.5 wt % agarose in DI water was pipetted into the open reservoir of the microfluidic device and solidified. Water containing 1.0 wt % rhodamine (0.48 kDa) was introduced into the microfluidic channels at a flowrate of 25 µL/min. Time-lapse fluorescent images, taken from beneath the microfluidic channels (FIG. 6A) show that a high fluorescent signal is initially localized within and immediately above the microfluidic channels, but that an overall increase in fluorescent intensity and broadening of high-intensity regions occurs with time, signifying vertical and lateral diffusion of the rhodamine from the microchannels into the neighboring hydrogel. Florescent intensity at two points—one directly beneath a PDMS wall and another centred beneath a microfluidic channel—was tracked over time. This data, normalized with respect to the maximum and minimum fluorescent intensity at 1 second, is represented in FIG. 6B.

Figure 6A:
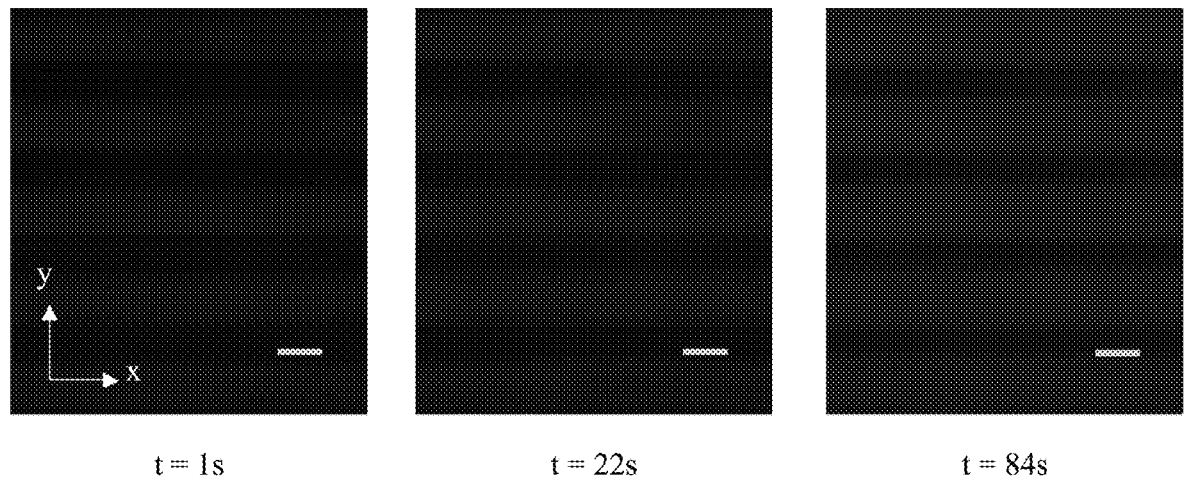
FIGS. 6A-F show graphs and images illustrating solute transport in microfluidic channels for different molecular weight molecules. (A) Shows time-lapse micrographs of fluorescent rhodamine solutions being driven through channels at flowrate of 25 µL/min, scale bar=100 µm. (B) Shows a graph illustrating normalized fluorescent intensity of the rhodamine solutions of (A) versus time. (C) Shows images illustrating numerical simulation of diffusion of small molecules from microfluidic channels (µC) into hydrogel over time. Dashed line represents boundary between µC and hydrogel; dimensions given in micrometers. (D) Shows a graph illustrating normalized concentration of the numerical simulations of (C) versus time. (E) Shows time-lapse micrographs of fluorescent FITC-Dextran solutions being driven through channels at flowrate of 25 µL/min, scale bar=100 µm. (F) Shows a graph illustrating normalized fluorescent intensity of the FITC-Dextran solutions of (E) versus time.
Figure 6B:
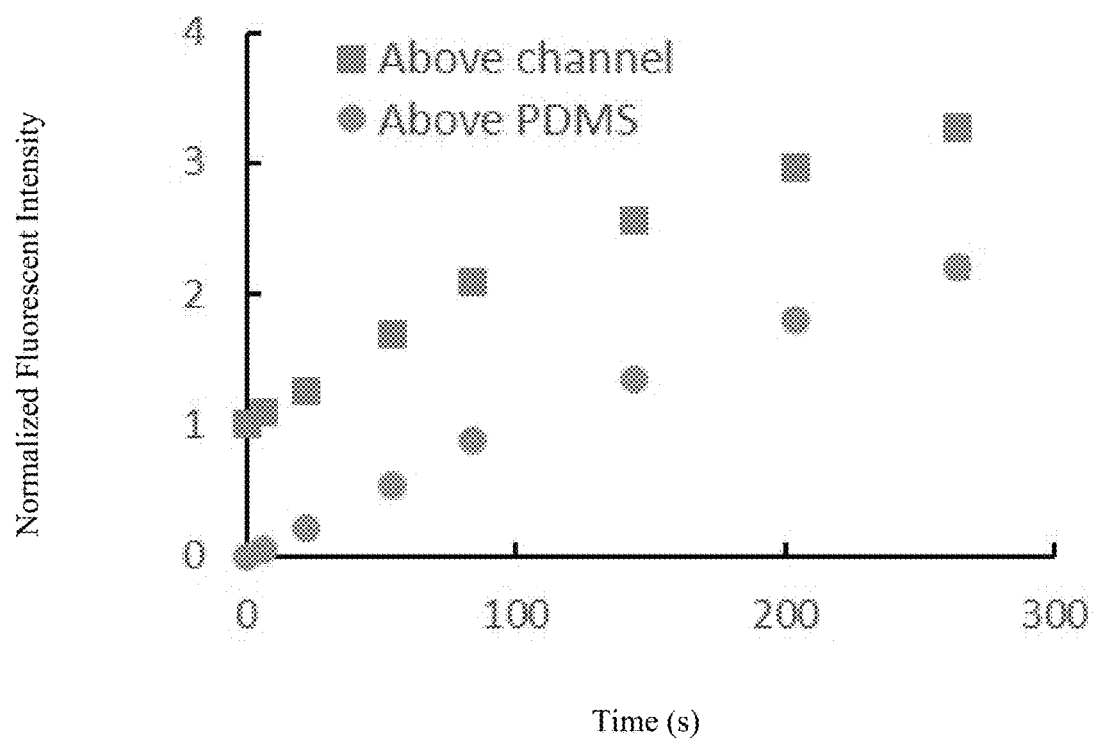
Figure 6C:
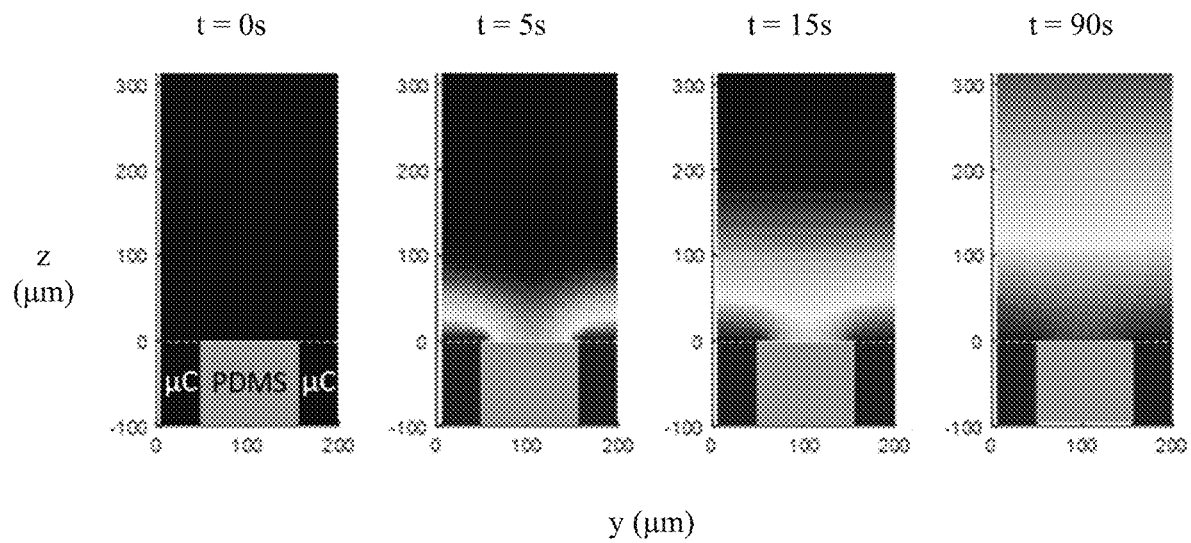

FIG. 6C shows the numerical solution of a comparable scenario developed using COMSOL software: transient diffusion of a chemical species from a constant concentration source—here, the microfluidic channels—into a region with an initial species concentration of zero. The diffusion coefficient of the species was modelled as $D=4\times10^{-6}$ cm$^2$/sec, in order to simulate rhodamine in a 1.5% agarose hydrogel medium. The data from each timepoint in the simulation was integrated along the z-direction to provide a source of comparison to the experimental results. For example, summing species concentration along the z-direction at $y=0$ correlates to total amount of the species present in a column above the midpoint of one of the microfluidic channels. This data was similarly normalized with respect to initial concentration in the hydrogel region and microchannel region, and used to generate the concentration versus time plot shown in FIG. 6D; "above channel" corresponds to $y=0$ while "above PDMS" corresponds to $y=100$ µm.

Figure 6D:
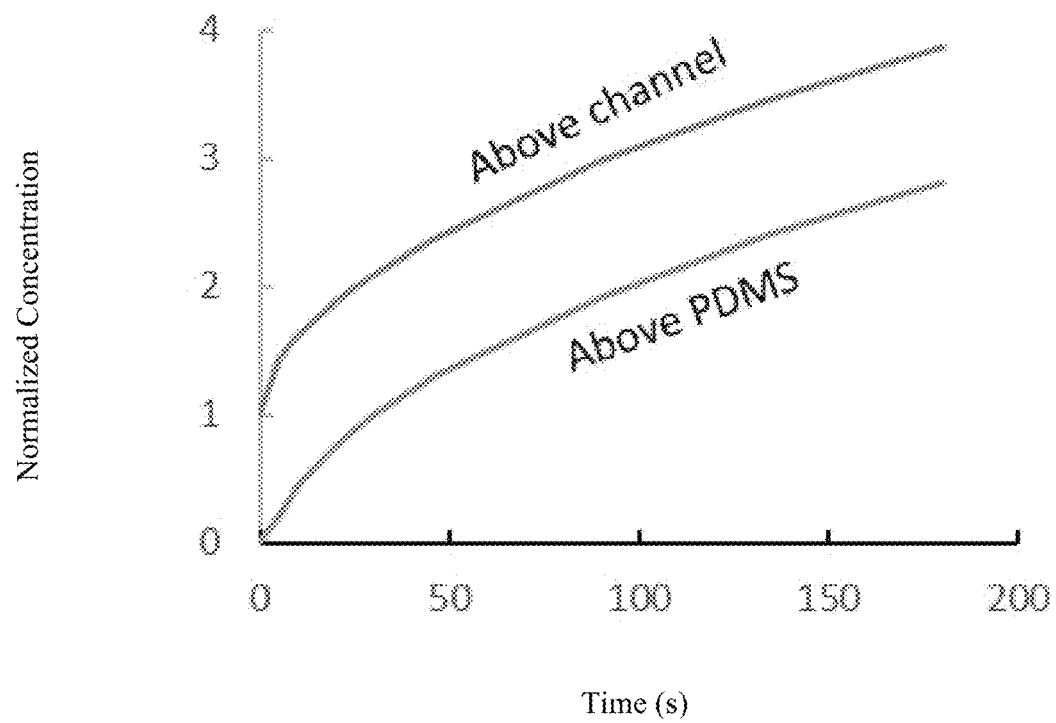
Figure 6E:
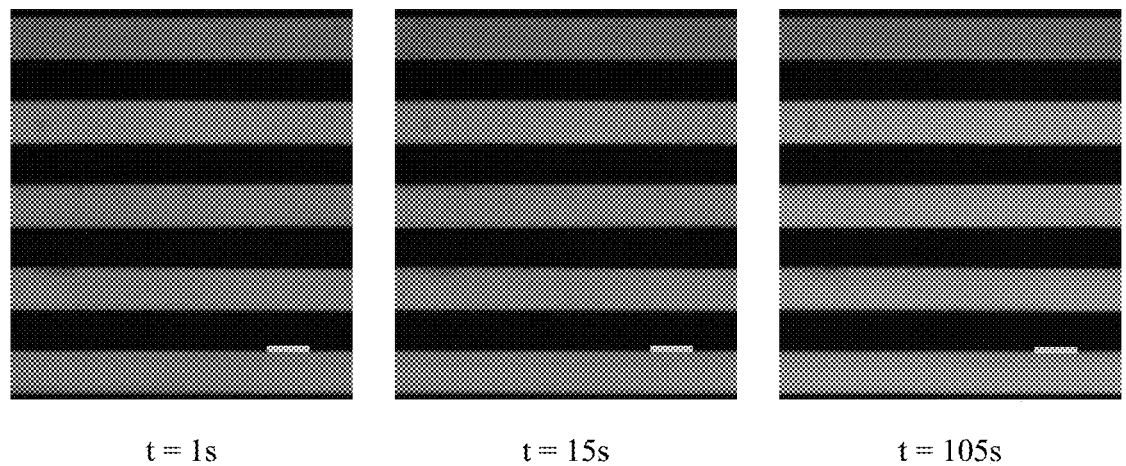
Figure 6F:
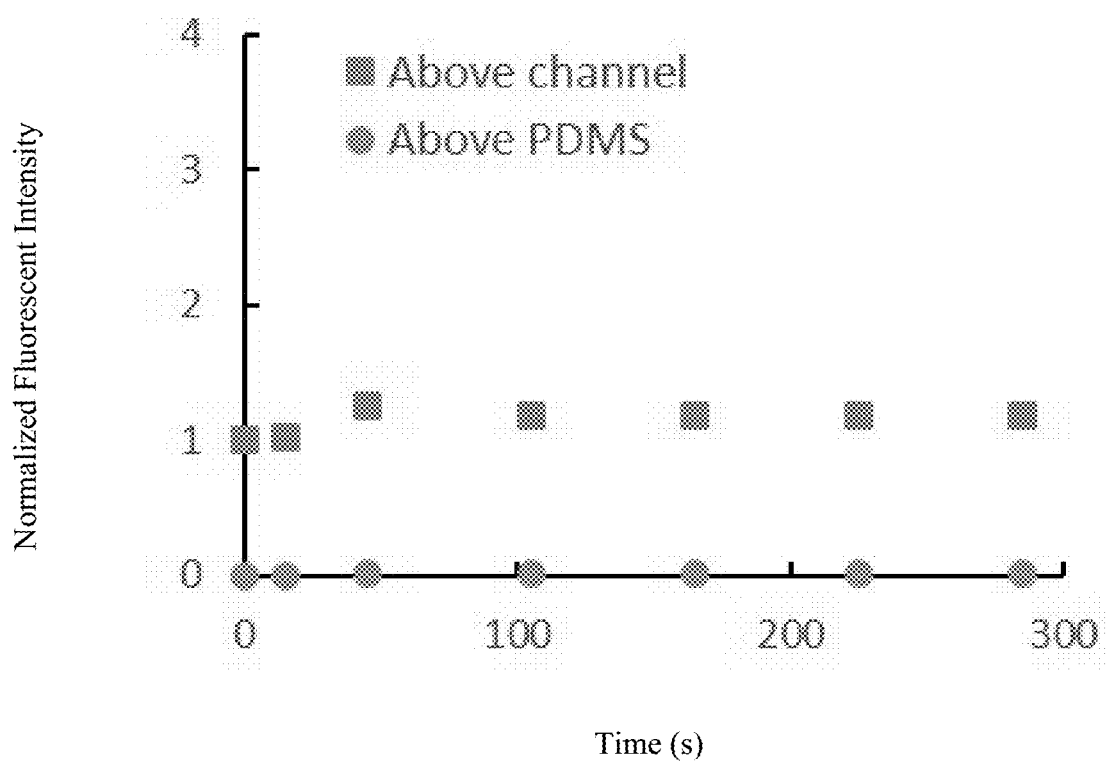

The intensity/time plot in FIG. 6B and concentration/time plot in FIG. 6D show very similar trends; additionally, incubating a PDMS surface in contact with a 1.5 wt % solution of rhodamine over 180 seconds showed no detectable diffusion of rhodamine into the PDMS. This information supports the conclusion that the fluorescent intensity increase seen in FIG. 6A is the result of unobstructed diffusion of rhodamine species from the microchannels into the adjacent hydrogel. The same experiment was repeated with a larger fluorescently-tagged species: a solution of FITC-dextran (2,000 kDa) in water was pumped through the microchannels of the device at 25 µL/min. In contrast to the relatively smaller rhodamine molecules, which diffused into the adjacent hydrogel, the much larger FITC-dextran molecules flowed freely through the channels but did not penetrate the hydrogel (FIGS. 6E-F), so there was no change in fluorescent intensity in the system over time. Because there was no detectable change in the fluorescent intensity of the hydrogel above the PDMS channels, this demonstrates sufficient sealing between the PDMS and agarose hydrogel to prevent seepage of fluid outside the defined microchannel geometry.

Three Dimensional Cell Culture in CB Microfluidic Device

Figure 7A:
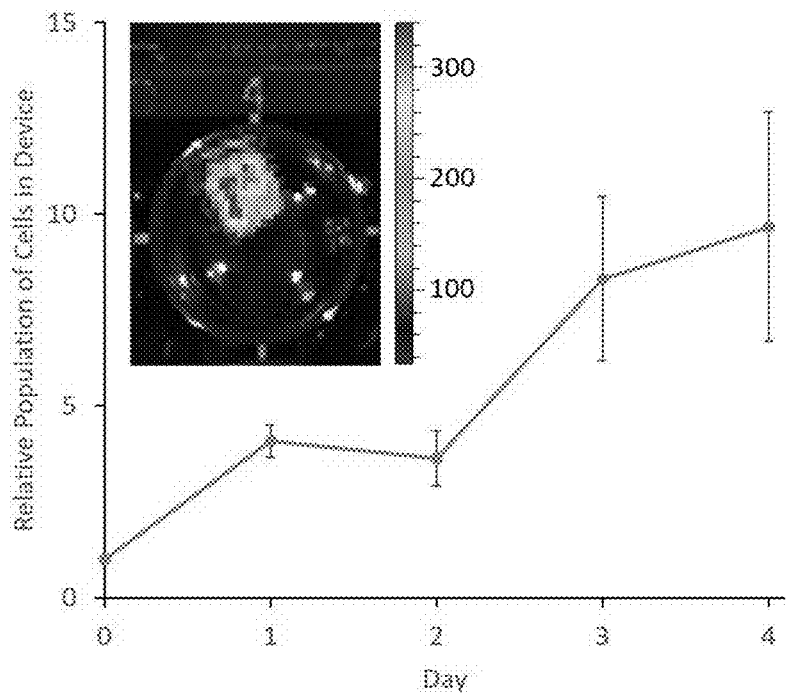
FIGS. 7A-C show a graph and images illustrating cell viability and sample removal in a microfluidic device according to an embodiment of the disclosure. (A) Shows a graph illustrating cell proliferation data for 3D cell culture of MDA-231 Luc-GFP cells in collagen in the microfluidic device; inset shows IVIS imaging of one cell/collagen suspension after being removed from the microfluidic device. (B) Shows an image illustrating MDA-MB 231 cells in microfluidic device after 3 days, scale bar=100 µm. (C) Shows an image of cell/collagen suspension retrieval after tissue culture, scale bar=5 mm.

In order to demonstrate the utility of the CB microfluidic device in cell culture applications, MDA-231 Luc-GFP cells were cultured in a collagen matrix within the device over a period of four days. A liquid collagen and cell mixture was prepared and pipetted into the reservoir of microfluidic devices and cured to solidify. The reservoirs of the microfluidic devices were then sealed using the removable lids and cell culture media was supplied through the microfluidic channels at a constant flowrate for the duration of the experiments. Cell proliferation was measured using IVIS imaging (inset, FIG. 7A) of cells after 24, 48, 72 or 96 continuous hours of culture in the devices. Cell proliferation data, shown in FIG. 7A, indicates that cells cultured in the CB microfluidic device show a 10× increase in cell population over the time period, indicating a viable and proliferative cell microenvironment within the device.

Figure 7B:
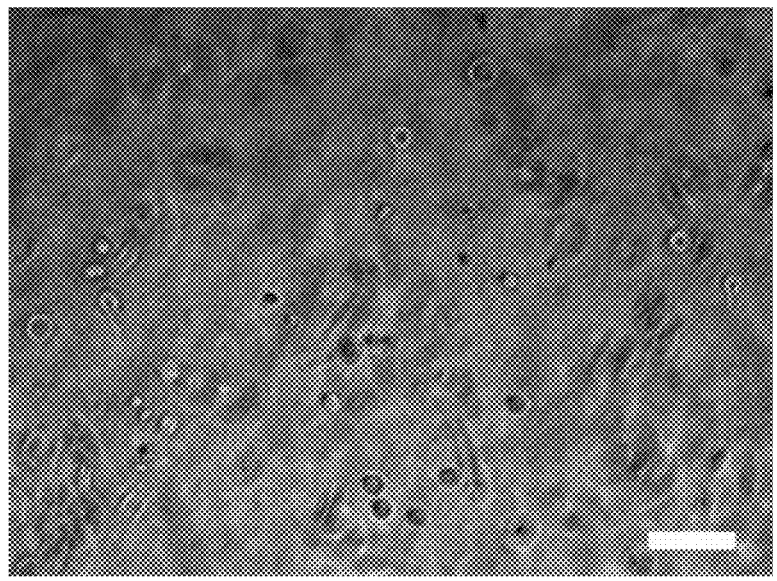
Figure 7C:
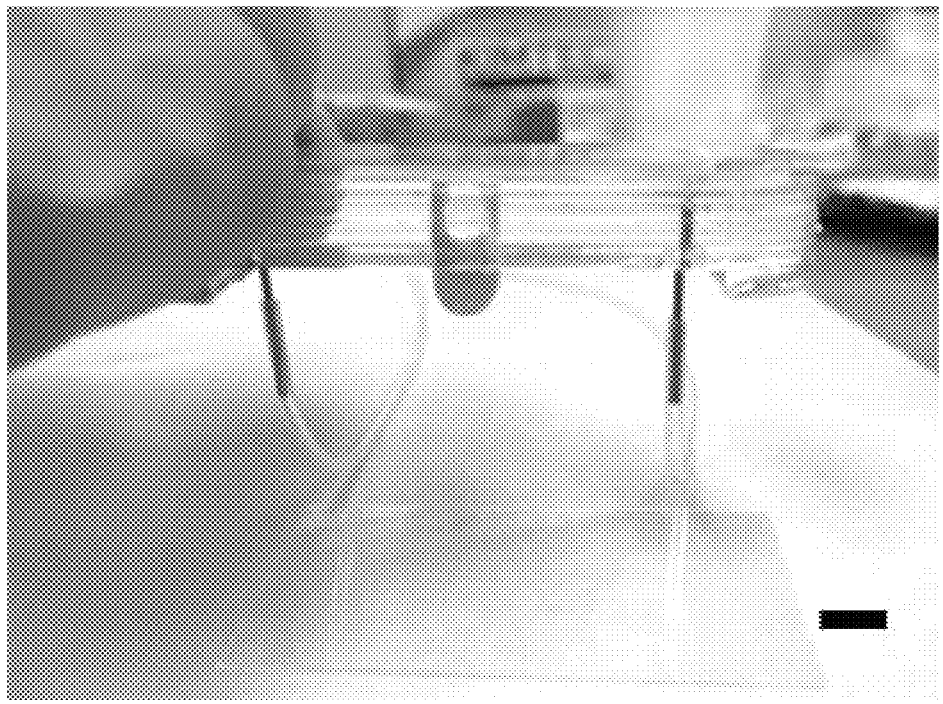

The channels of the CB microfluidic device are created from optically transparent PDMS, making it possible to observe cells inside the device during culture (FIG. 7B). In addition, using CB surfaces to integrate 3D cell culture with microfluidic channels also makes it possible to easily retrieve cells after culture. This is in contrast to many microfluidic devices, which typically require cells to be introduced into the device via fluid ports; once cells are cultured in these systems it can be challenging to retrieve the cells without damage. To retrieve cells in the CB microfluidic device, the vacuum holding the removable lid to the device is released and the lid is removed from the device. Then a small amount of back pressure is applied to the fluidic inlet; this generates enough force to gently remove the cell/hydrogel plug from the reservoir (FIG. 7C). The cells can then be captured and are readily available for further analysis.

CONCLUSIONS

This Example shows that careful design of micropatterned surfaces to induce Cassie-Baxter mode can be used to integrate 3D cell culture and microfluidic fluid delivery. The use of CB mode integration eliminates the need for a mechanical boundary between the hydrogel and microfluidic channels, which provides a faster, more direct pathway for diffusive transfer between the hydrogel and bulk fluid than is present in commercially-available transwell plate systems or membrane-associated microfluidic devices. This reversible integration makes it easy to recover the cells after culture, enabling additional post-culture analyses. Moreover, because the integration step only requires simple pipetting of the 3D matrix onto the open channels without the need for complex new protocols, it provides an attractive option for adoption into many tissue culture labs.

All publications, patents, and patent applications mentioned in this specification are herein incorporated by reference to the same extent as if each individual publication, patent, or patent application was specifically and individually indicated to be incorporated by reference, including the references set forth in the following list:

REFERENCES

1. Edmondson, R., et al., *Three-Dimensional Cell Culture Systems and Their Applications in Drug Discovery and Cell-Based Biosensors*. ASSAY and Drug Development Technologies, 2014. 12(4): p. 207-218.
2. Tibbitt, M. W. and K. S. Anseth, *Hydrogels as Extracellular Matrix Mimics for 3D Cell Culture*. Biotechnology and Bioengineering, 2009. 103(4): p. 655-663.
3. Xiong, G., et al., *Development of an ex vivo breast cancer lung colonization model utilizing a decellularized lung matrix*. Integrative Biology, 2015. 7(12): p. 1518-1525.
4. Kim, M. S., J. H. Yeon, and J.-K. Park, *A microfluidic platform for 3-dimensional cell culture and cell-based assays*. Biomed Microdevices, 2007. 9: p. 25-34.
5. Vickerman, V., et al., *Design, fabrication and implementation of a novel multi parameter control Microfluidic Platform for Three-Dimensional Cell Culture and Real-Time Imaging*. Lab Chip, 2008. 8(9): p. 1468-1477.
6. Bettinger, C., J. T. Borenstein, and S. L. Tao, *Microfluidic Platforms for Evaluating Angiogenesis and Vasculogenesis*, in *Microfluidic Cell Culture Systems*. 2012, Elsevier. p. 385-405.
7. Song, J. W., et al., *Microfluidic Endothelium for Studying the Intravascular Adhesion of Metastatic Breast Cancer Cells*. PLoS ONE, 2009. 4(6): p. e5756.
8. Shin, M. K., S. K. Kim, and H. Jung, *Integration of intra-and extravasation in one cell-based microfluidic chip for the study of cancer metastasis*. Lab on a Chip, 2011. 11: p. 3880-3887.
9. Huang, C. P., et al., *Engineering microscale cellular niches for three-dimensional multicellular co-cultures*. Lab on a Chip, 2009. 9(12): p. 1740-1748.
10. Chrobak, K. M., D. R. Potter, and J. Tein, *Formation of perfused, functional microvascular tubes in vitro*. Microvascular Research, 2006. 71: p. 185-196.
11. Chung, S., et al., *Cell migration into scaffolds under co-culture conditions in a microfluidic platform*. Lab on a Chip, 2008: p. 1-8.
12. Haessler, U., et al., *Migration dynamics of breast cancer cells in a tunable 3D interstitial flow chamber*. Integrative Biology, 2012. 4: p. 401-409.
13. Liu, M. and Q. Chen, *Characterization study of bonded and unbonded polydimethylsiloxane aimed for bio-microelectromechanical systems-related applications*. J. Micro/Nanolith. MEMS MOEMS, 2007. 6(2).
14. Kim, H. T. and O. C. Jeong, *PDMS surface modification using atmospheric pressure plasma*. Microelectronic Engineering, 2011.8: p. 2281-2285.
15. Tan, S.-H., N.-T. Nguyen, and Y. C. Chua, *Oxygen plasma treatment for reducing hydrophobicity of a sealed polydimethylsiloxane microchannel*. BIOMICROFLUIDICS, 2010. 4(3).
16. Huh, D., et al., *Reconstituting Organ-Level Lung Functions on a Chip*. Science, 2010. 328.
17. Pries, A. R. and W. M. Kuebler, *The Vascular Endothelium I (Normal Endothelium)*, in *Handbook of Experimental Pharmacology*. 2006, Springer. p. 1-40.
18. Toh, Y.-C., et al., *A microfluidic 3D hepatocyte chip for drug toxicity testing*. Lab on a Chip, 2009. 9.
19. Ling, Y., et al., *A cell-laden microfluidic hydrogel*. Lab on a Chip, 2007. 7: p. 756-762.
20. Cheng, S.-Y., et al., *A hydrogel-based microfluidic device for the studies of directed cell*. Lab on a Chip, 2007. 7: p. 763-769.
21. Golden, A. P. and J. Tien, *Fabrication of microfluidic hydrogels using molded gelatin as a sacrificial element*. Lab on a Chip, 2007. 7: p. 720-725.
22. Zervantonakis, I. K., et al., *Microfluidic devices for studying heterotypic cell-cell interactions and tissue specimen cultures under controlled microenvironment*. Biomicrofluidics, 2011. 5.
23. Miller, J. S., et al., *Rapid casting of patterned vascular networks for perfusable engineered three-dimensional tissues*. Nature Materials, 2012. 11: p. 738-774.
24. Lee, W., et al., *On-Demand Three-Dimensional Freeform Fabrication of Multi-Layered Hydrogel Scaffold With Fluidic Channels*. Biotechnology and Bioengineering, 2010. 105(6): p. 1178-1186.
25. Wang, X.-Y., et al., *Engineering interconnected 3D vascular networks in hydrogels using molded sodium alginate lattice as the sacrificial template*. Lab on a Chip, 2014. 14: p. 2709-2716.
26. Whyman, G., E. Bormashenko, and T. Stein, *The rigorous derivation of Young, Cassie-Baxter and Wenzel equations and the analysis of the contact angle hysteresis phenomenon*. Chemical Physics Letter, 2008. 450: p. 355-359.
27. Patankar, N. A., *Mimicking the Lotus Effect: Influence of Double Roughness Structures and Slender Pillars*. Langmuir, 2004. 20: p. 8209-8213.
28. Liu, K., X. Yao, and L. Jiang, *Recent developments in bio-inspired special wettability*. Chemical Society Reviews, 2010. 39: p. 3240-3255.
29. Varansi, K. K., et al. *Design of Superhydrophobic Surfaces for Optimum Roll-off and Droplet Impact Resistance*. in *ASME International Mechanical Engineering Congress and Exposition*. 2008. Boston.

30. Milne, A. J. B. and A. Amirfazli, *The Cassie equation: How it is meant to be used.* Advances in Colloid and Interface Science, 2012. 170: p. 48-55.
31. Kim, H. T. and O. C. Jeong, *PDMS surface modification using atmospheric pressure plasma.* Microelectronic Engineering, 2011. 88(8): p. 2281-2285.
32. Pluen, A., et al., *Diffusion of macromolecules in agarose gels: comparison of linear and globular configurations.* Biophysical journal, 1999. 77(1): p. 542-552.
33. Gendron, P.-O., F. Avaltroni, and K. J. Wilkinson, *Diffusion Coefficients of Several Rhodamine Derivatives as Determined by Pulsed Field Gradient—Nuclear Magnetic Resonance and Fluorescence Correlation Spectroscopy.* Journal of Fluorescence, 2008. 18(6): p. 1093.

While the disclosure is susceptible to various modifications and alternative forms, specific embodiments thereof have been shown by way of example in the drawings and are herein described below in detail. It should be understood, however, that the description of specific embodiments is not intended to limit the disclosure to cover all modifications, equivalents and alternatives falling within the spirit and scope of the disclosure as defined by the appended claims.

What is claimed is:

1. A tissue culture device comprising:
    a microfluidic layer including at least one hydrophobic microchannel;
    an inlet in fluid communication with the at least one hydrophobic microchannel;
    an outlet in fluid communication with the at least one hydrophobic microchannel; and
    a reservoir portion over the at least one hydrophobic microchannel, the reservoir portion including an opening aligned with an uncovered portion of the at least one hydrophobic microchannel;
    wherein the at least one hydrophobic microchannel prevents a solution in the opening of the reservoir portion from filling the at least one hydrophobic microchannel through the uncovered portion;
    wherein the inlet and the outlet provide fluid flow into and out of the at least one hydrophobic microchannel without passing through the opening; and
    wherein, when a material is present in the opening, a fluid introduced to the inlet flows through the at least one hydrophobic microchannel and directly contacts the material before exiting through the outlet.

2. The device of claim 1, wherein the at least one hydrophobic microchannel comprises a Cassie-Baxter mode surface.

3. The device of claim 1, wherein the at least one hydrophobic microchannel comprises a material selected from the group consisting of polydimethylsiloxane (PDMS), polystyrene, surface-treated glass, and combinations thereof.

4. The device of claim 1, wherein the at least one hydrophobic microchannel comprises a surface treated surface.

5. The device of claim 4, wherein the surface treated surface comprises increased surface roughness.

6. The device of claim 1, wherein the at least one hydrophobic microchannel comprises a feature height (h) that is greater than the minimum feature height for sustaining Cassie-Baxter mode ($h_{crit}$);
    wherein $h_{crit}$ is defined as $$h_{crit} = -\frac{b}{2}\left(\frac{\cos\theta_e + 1}{\cos\theta_e}\right);$$

wherein b is the width of cavities in the at least one hydrophobic microchannel; and
    wherein $\theta_e$ is the angle of contact between the at least one hydrophobic microchannel and a liquid in the reservoir portion.

7. The device of claim 1, wherein the reservoir portion comprises a material selected from the group consisting of polydimethylsiloxane (PDMS), polystyrene, surface-treated glass, and combinations thereof.

8. The device of claim 1, wherein the reservoir portion and the at least one hydrophobic microchannel comprise the same material.

9. The device of claim 1, wherein the reservoir portion and the at least one hydrophobic microchannel comprise different materials.

10. The device of claim 1, wherein the device is devoid of any material separating the uncovered portion of the at least one hydrophobic microchannel from the opening in the reservoir portion.

11. The device of claim 1, wherein the at least one hydrophobic microchannel comprises multiple hydrophobic microchannels.

12. The device of claim 11, wherein a shape and geometry of the hydrophobic microchannels mimics the shape and geometry of blood vessels in a capillary network.

13. A method of culturing tissue, the method comprising:
    providing the device of claim 1;
    introducing a cell solution into the opening in the reservoir portion;
    solidifying the cell solution in the reservoir portion;
    positioning a removable lid over the opening in the reservoir portion; and
    providing a flow of fluid through at least one hydrophobic microchannel;
    wherein the at least one hydrophobic microchannel prevents the cell solution from flooding the at least one hydrophobic microchannel during the introducing step.

14. The method of claim 13, wherein the fluid comprises cell culture media.

15. The method of claim 14, wherein the cell culture media flowing through the at least one hydrophobic microchannel is in direct contact with the cell solution.

16. The method of claim 15, wherein the direct contact provides diffusion-based solute exchange between the cell culture media and the cell solution.

* * * * *